US006608038B2

(12) United States Patent
Caplan et al.

(10) Patent No.: US 6,608,038 B2
(45) Date of Patent: Aug. 19, 2003

(54) METHODS AND COMPOSITIONS FOR TREATMENT OF DIABETES AND RELATED CONDITIONS VIA GENE THERAPY

(75) Inventors: Shari L. Caplan, Sloatsburg, NY (US); Brian R. Boettcher, Morristown, NJ (US); Eric D. Slosberg, New York, NY (US); Sheila Connelly, Ijamsville, MD (US); Michael Kaleko, Rockville, MD (US); Urvi J. Desai, Germantown, MD (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/808,457

(22) Filed: Mar. 14, 2001

(65) Prior Publication Data

US 2002/0065239 A1 May 30, 2002

Related U.S. Application Data

(60) Provisional application No. 60/266,328, filed on Mar. 15, 2000.

(51) Int. Cl.$^7$ .................. A61K 31/70; C07H 21/04; C12N 15/74; C12N 15/85; C12N 5/02
(52) U.S. Cl. ............... 514/44; 435/320.1; 435/325; 435/455; 536/23.1
(58) Field of Search ............... 514/44; 435/320.1, 435/325, 455; 536/23.1

(56) References Cited

PUBLICATIONS

Grimsby et al. Characterization of glucokinase regulatory protein–deficient mice pp. 7826–7830 2000 vol. 275 No. 11.*
Bosco et al. Glucokinase and glucokinase regulatory protein: mutual dependence for nuclear localization pp. 215–222 2000.*
Freeman et al. Present and potential future use of gene therapy for the treatment of non–insulin dependent diabetes mellitus (review) pp. 585–592 1999.*
Levine et al. Towards gene therapy of diabetes mellitus pp. 165–171 vol. 5, 1999.*
Tiedge et al. Metabolic regulation, activity state, and intracellular binding of glucokinase in insulin–secreting cells pp. 514–523 1999.*
Mooktiar et al. Heterologous expression and characterization of rat liver glucokinase regulatory protein pp. 1670–1677 vol. 45 1996.*
Warner et al. Human glucokinase regulatory protein (GCKR): cDNA and genomic cloning, complete primary structure, and chromosomal localization pp. 532–536 1995.*

Robbins et al, Pharmacol Ther 1998;80:35–47.*
Baque et al., Biochem J. vol. 304, pp 1009–1014.
Brown et al., Diabetes, vol. 46, pp. 179–186 (1997).
Chillaron et al., FASEB J., vol. 13, pp. 2153–2160 (1999).
De la Iglesia et al., FEBS Letters, vol. 456, pp. 332–338 (1999).
Dang et al., Gene Therapy and Translational Cancer Therapy, Clinical Cancer Research, vol. 5, 471–474, Feb. 1999.
Eck, S.L. et al., Ch 5. Gene Based Therapy, Goodman Gillman's The Pharmacological basis of Therapeutics, pp 77–101, (1996).
Farrelly et al. PNAS 1, vol. 96, No. 25, pp. 14511–14516 (1999).
Fernandez–Novell et al., FEBS Letters, vol. 459, pp. 211–214 (1999).
Ghilardi et al., Proc. Natl. Acad. Set. USA, vol. 93, pp. 6231–6235 (1996).
Gomez–Foix, The Journal of Biological Chemistry, vol. 267, No. 35, pp 25129–25134 (1992).
Grimsby et al., The Journal of Biological Chemistry, vol. 275, No. 11, pp. 7826–7831 (2000).
He et al., Gene, vol. 175, pp. 121–125 (1996).
Morsy et al., Molecular Medicine Today, vol. 5, pp. 18–24 (1999).
Sher et al., Biochemistry, vol. 32, pp. 5598–5604 (1993).
Shiota et al., Diabetes, vol. 47, pp. 867–873 (1998).
Tanizawa et al, Proc. Natl. Acad. Sci. USA, vol. 88, pp. 7294–7297 (1991).
Van Schaftingen et al., Advan. Enzyme Regul., vol. 32, pp 133–148 (1992).
Warner et al., Mammalian Genome, vol. 6, pp. 532–536 (1995).

* cited by examiner

*Primary Examiner*—Anne M. Wehbe'
*Assistant Examiner*—Janice Li
(74) *Attorney, Agent, or Firm*—Gregory D. Ferraro

(57) ABSTRACT

Disclosed are methods and compositions for treatment of diabetes, obesity and diabetic-related conditions. The methods include gene therapy based administration of a therapeutically effective amount of vectors encoding the following: glucokinase regulatory protein alone or co-administered with glucokinase or with metabolism modifying proteins; glucokinase co-administered with metabolism modifying proteins; or glucokinase regulatory protein co-administered with glucokinase in combination with metabolism modifying proteins, to a diabetic patient. Wherein the metabolism modifying proteins include UCP2, UCP3, PPARα, OB-Rb, GLP-1 and GLP-1 analogs (administered via vector or directly as a peptide). Preferred examples of GLP-1 analogs include GLP-1-Gly8, Extendin-4 and the "Black Widow" chimeric GLP-1 analog. Additionally, PPARα ligands and DPP-IV inhibitors may be co-administered with the above.

8 Claims, 21 Drawing Sheets

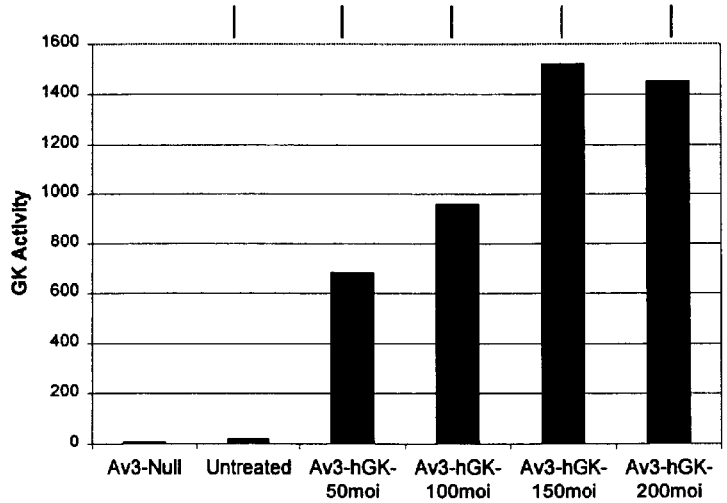
Figure 5

| Before the treatment | Glucose (mg/dl) | Lactate (mg/dl) | FFA (mmol/l) | TG (mg/dl) | ALT (U/l) | Insulin (ng/ml) |
|---|---|---|---|---|---|---|
| HF Untreated | 182±26 | 37±7.9 | 1.05±0.16 | 87.5±22.6 | 51.5±48.5 | 2.01±1.77 |
| HF Av3Null | 186±26 | 33±11.6 | 1.04±0.10 | 95.3±22 | 67.5±34.8 | 1.61±0.87 |
| HF Av3hGK | 174±29 | 34±8.2 | 1.14±0.16 | 90±18.8 | 87.5±65.1 | 1.84±1.03 |
| 3 Weeks after the treatment | Glucose (mg/dl) | Lactate (mg/dl) | FFA (mmol/l) | TG (mg/dl) | ALT (U/l) | Insulin (ng/ml) |
| HF Untreated | 177±30 | 34.9±8.7 | 1.14±0.23 | 71.1±14.3 | 56.8±46.7 | 1.79±1.17 |
| HF Av3Null | 160±21 | 33.4±15.2 | 1.65±0.15 | 120±105 | 153.4±125.3 | 1.53±0.96 |
| HF Av3hGK | 127±26 | 33.9±13.7 | 1.21±0.12 | 84.9±27.7 | 275.4±118.3 | 0.64±0.26 |

| Before the treatment | Glucose (mg/dl) | Lactate (mg/dl) | FFA (mmol/l) | TG (mg/dl) | ALT (U/l) | Insulin (ng/ml) |
|---|---|---|---|---|---|---|
| LF Untreated | 102±21 | 29.0±7.1 | 1.61±0.20 | 118.8±26.2 | 28.4±30.8 | 0.81±0.22 |
| LF Av3Null | 95±21 | 34.3±3.1 | 1.51±0.22 | 97±15.9 | 66.2±90.4 | 0.37±0.35 |
| LF Av3hGK | 137±24 | 40.6±11.8 | 1.25±0.08 | 92±16.2 | 67.6±43.1 | 0.99±0.86 |
| 3 weeks after the treatment | Glucose (mg/dl) | Lactate (mg/dl) | FFA (mmol/l) | TG (mg/dl) | ALT (U/l) | Insulin (ng/ml) |
| LF Untreated | 93±15 | 22.4±6.4 | 1.58±0.26 | 87.8±23.6 | 44.8±31.3 | 0.46±0.26 |
| LF Av3Null | 119±18 | 24.3±9.0 | 1.27±0.47 | 68.6±18.3 | 118±37.2 | 0.54±0.13 |
| LF Av3hGK | 121±34 | 25.5±6.9 | 1.45±0.34 | 85±24.8 | 97±64.1 | 0.51±0.43 |

Figure 7

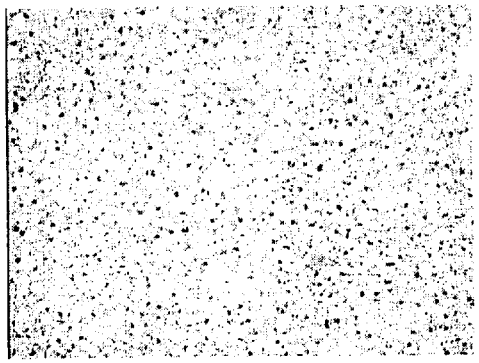 HBSS
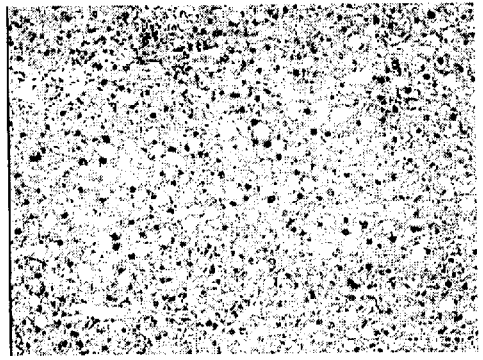 Av3-Null
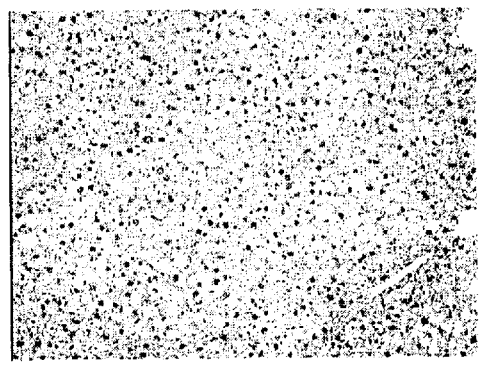 Av3-GKRP
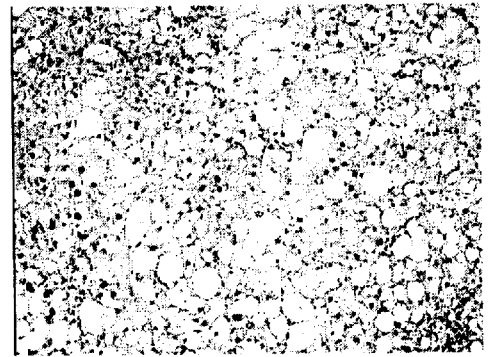 Av3-GK
Figure 9

METHODS AND COMPOSITIONS FOR TREATMENT OF DIABETES AND RELATED CONDITIONS VIA GENE THERAPY

This application claims priority under 35 U.S.C. §119(e) to U.S. Provisional Application No. 60/266,328 filed Mar. 15, 2000 now abandoned.

BACKGROUND

There are 15.7 million people or 5.9% of the population in the United States who have diabetes. While an estimated 10.3 million have been diagnosed, unfortunately, 5.4 million people are not aware that they have the disease. Each day approximately 2,200 people are diagnosed with diabetes. About 798,000 people will be diagnosed this year.

Diabetes is the seventh leading cause of death (sixth-leading cause of death by disease) in the United States. Based on death certificate data, diabetes contributed to more than 187,000 deaths in 1995. Diabetes is a chronic disease that has no cure.

Many people first become aware that they have diabetes when they develop one of its life-threatening complications. Diabetes is the leading cause of new cases of blindness in people ages 20–74. Each year, from 12,000 to 24,000 people lose their sight because of diabetes. Diabetes is the leading cause of end-stage renal disease, accounting for about 40% of new cases. In 1995, approximately 27,900 people initiated treatment for end stage renal disease (kidney failure) because of diabetes. About 60–70 percent of people with diabetes have mild to severe forms of diabetic nerve damage, which, in severe forms, can lead to lower limb amputations. In fact, diabetes is the most frequent cause of non-traumatic lower limb amputations. The risk of a leg amputation is 1540 times greater for a person with diabetes. Each year, more than 56,000 amputations are performed among people with diabetes. People with diabetes are 2 to 4 times more likely to have heart disease which is present in 75 percent of diabetes-related deaths (more than 77,000 deaths due to heart disease annually). They are also 2 to 4 times more likely to suffer a stroke.

Diabetes is a disease in which the body does not produce or properly use insulin, a hormone that is needed to convert sugar, starches and other food into energy needed for daily life. The cause of diabetes is a mystery, although both genetics and environmental factors such as obesity and lack of exercise appear to play roles. There are two major types of diabetes, Type 1, which is an autoimmune disease in which the body does not produce any insulin, most often occurring in children and young adults, and Type 2, which is a metabolic disorder resulting from the body's inability to make enough, or properly use, insulin. People with type 1 diabetes must take daily insulin injections to stay alive. Type 1 diabetes accounts for 5–10 percent of diabetes. Type 2 diabetes is the most common form of the disease accounting for 90–95 percent of diabetes. Type 2 diabetes is nearing epidemic proportions, due to an increased number of older Americans, and a greater prevalence of obesity and a sedentary lifestyle.

Impaired glucose homeostasis (or metabolism) refers to a condition in which blood sugar levels are higher than normal but not high enough to be classified as diabetes. There are two categories that are considered risk factors for future diabetes and cardiovascular disease. Impaired glucose tolerance (IGT) occurs when the glucose levels following a 2-hour oral glucose tolerance test are between 140 to 199 mg/dl. IGT is a major risk factor for type 2 diabetes and is present in about 11 percent of adults, or approximately 20 million Americans. About 4045 percent of persons age 65 years or older have either type 2 diabetes or IGT. Impaired fasting glucose (IFG) occurs when the glucose levels following an 8-hour fasting plasma glucose test are greater than 110 but less than 126 mg/dl.

The total annual economic cost of diabetes in 1997 was estimated to be $98 billion dollars. That includes $44.1 billion in direct medical and treatment costs and $54 billion for indirect costs attributed to disability and mortality.

The direct and indirect costs of diabetes are high. In 1997, total health expenditures incurred by people with diabetes amounted to $77.7 billion, including health care costs not resulting from diabetes. The per capita costs of health care for people with diabetes amounted to $10,071 while health care costs for people without diabetes amounted to $2,699 in 1997. [Information obtained from the American Diabetes Association.]

Hyperglycemia, a common feature of diabetes, is caused by decreased glucose utilization by liver and peripheral tissues and an increased glucose production by liver. Glucokinase (GK), the major glucose phosphorylating enzyme in the liver and the pancreatic β-cells, plays an important role in regulating blood glucose homeostasis. Notably, the levels of this enzyme are lowered in patients with type 2 diabetes (Caro, J. F. et al., Hormone metabolic Res. 27;19–22,1995) and in some diabetic animal models (Barzilai, N. and Rossetti, L. J. Biol. Chem. 268:25019–25025). Studies involving transgenic diabetic mice have shown that increased GK copy number results in increased hepatic glucose metabolism and decreased plasma glucose levels (Ferre, T. et al., Proc. Natl. Acad. Sci. USA 93:7225–7230, 1996a and FASEB J. 10:1213–1218, 1996b; Niswender, K. D. et al., J. Biol. Chem. 272:22570–22575, 1997), demonstrating that increasing liver GK may be effective in reducing hyperglycemia in diabetes. In addition, Hariharan, N. et al., (Diabetes 46:11–16, 1997) have demonstrated that increasing liver GK improves glucose homeostasis and leads to weight reduction in transgenic mice.

An approach to increase liver GK activity is to relieve its inhibition by the glucokinase regulatory protein ("GKRP") (e.g. decrease GKRP expression). Van Schaftingen and coworkers were the first to identify GKRP and suggested that it might play a role in control of liver GK activity (Van Schaftingen, E. et al., Adv. Enzyme Regul. 32:133–148, 1992). They demonstrated that GKRP binds to GK and inhibits its activity and that fructose-6-phosphate (F-6-P) increases the inhibition of GK by binding to GKRP. This inhibition is reversed by the binding of fructose-1-phosphate (F-1-P) to GKRP (Vandercammen, A. et al., Biochem. J. 286:253–256, 1992 and Van Schaftingen, E. et al., FASEB J. 8:414419, 1994). Various groups have also demonstrated that GKRP binds to GK in the hepatocyte nucleus and may therefore function in vivo to regulate GK activity (Brown, K. S. et al., Diabetes 46:179–186, 1997; De la Iglesia, N. et al., FEBS Left. 456:332–338,1999; Fernandez-Novell, J. M. et al., FEBS Left. 459:211–214, 1999). The relevance of this mechanism in an in vivo setting has been demonstrated in experiments by Cherrington and coworkers (Shiota, M. et al., Diabetes 47:867–873, 1998). In these studies, small amounts of fructose, which is converted to fructose-1-phosphate in the liver and thus should increase free GK, substantially increased net hepatic glucose utilization, analogous to what is seen in the transition from fasted to fed states.

For the foregoing reasons, there is a need for new therapeutic treatments for diabetes; particularly by increasing GK activity.

There is also a need for other combinations of peptides and compounds and methods of their use for treating diabetes and diabetes-related conditions.

SUMMARY

Toward these ends and others, in one aspect the present invention there is provided a method of treating diabetes and diabetes-related conditions comprising administering to a subject in need thereof a therapeutically effective amount of a polynucleotide sequence encoding 1) GKRP or 2) GKRP in combination with a polynucleotide sequence encoding GK.

In another aspect, the present invention provides a method of treating diabetes and diabetes-related conditions comprising administering to a subject in need thereof a therapeutically effective amount of a polynucleotide sequence encoding one or more metabolism modifying proteins and peptides in combination with a polynucleotide sequence encoding 1) GK or 2) GKRP or 3) GKRP in combination with GK. Preferred metabolism modifying proteins and peptides include uncoupling proteins 2 and 3 ("UCP2 and UCP3"), peroxisome proliferator-activated receptor α ("PPARα"), the long form of the leptin receptor ("OB-Rb"), glucagon-like peptide 1 ("GLP-1") alone or in combination with a dipeptidyl peptidase IV ("DPP-IV") inhibitor and GLP-1 analogs. Preferred examples of GLP-1 analogs include GLP-1-Gly8, Extendin4, "Black Widow" chimeric GLP-1 analog.

In accordance with the above aspects of the invention, additional compounds may be co-administered with the combinations of proteins and peptides. The compounds include, but are not limited to, PPARα ligands and DPP-IV inhibitors.

The diabetes and diabetes-related conditions which are treated by the above-described methods include, but are not limited to, diabetes characterized by the presence of elevated blood glucose levels, such as hyperglycemic disorders, for example, diabetes mellitus, including both type 1 and type 2 diabetes as well as other diabetic-related disorders such as obesity, increased cholesterol, kidney-related disorders, decreased liver GK activity and the like. The above-described methods may be employed to lower insulin levels, improve glucose tolerance, increase hepatic glucose utilization, normalize blood glucose levels, increase apo A-I and HDL levels, decrease fibrinogen levels, stimulate hepatic fatty acid oxidation, reduce hepatic triglyceride accumulation and normalize glucose tolerance.

In another aspect the present invention provides a vector comprising a polynucleotide sequence(s) encoding GKRP or GKRP in combination with GK. In another embodiment of this aspect of the invention there is provided a vector comprising a polynucleotide sequence(s) encoding one or more metabolism modifying proteins and peptides in combination with a polynucleotide sequence encoding 1) GK or 2) GKRP or 3) GKRP in combination with GK.

In accordance with yet another aspect of the present invention there is provided a method of expressing 1) GKRP or 2) GKRP in combination with GK, comprising transducing cells in vivo with a vector comprising a polynucleotide sequence(s) encoding 1) GKRP or 2) GKRP in combination with GK, such that the cells are modified to produce the respective proteins and peptides.

In accordance with still another aspect of the present invention there is provided a method of expressing one or more metabolism modifying proteins and peptides in combination with 1) GK or 2) GKRP or 3) GKRP in combination with GK, comprising transducing cells in vivo with a vector comprising a polynucleotide sequence(s) encoding one or more metabolism modifying proteins and peptides in combination with a polynucleotide sequence encoding 1) GK or 2) GKRP or 3) GKRP in combination with GK, such that the cells are modified to produce the respective proteins and peptides.

In accordance with still another aspect of the present invention there is provided a pharmaceutical composition comprising vectors comprising a polynucleotide sequence(s) encoding 1) GKRP or 2) GKRP in combination with GK and a pharmaceutically acceptable carrier suitable for administration to a subject. In accordance with this aspect of the invention there is provided a pharmaceutical composition comprising vectors comprising a polynucleotide sequence(s) encoding one or more metabolism modifying proteins and peptides in combination with a polynucleotide sequence encoding 1) GK or 2) GKRP or 3) GKRP in combination with GK and a pharmaceutically acceptable carrier suitable for administration to a subject.

Other objects, features, advantages and aspects of the present invention will become apparent to those of skill from the following description, appended claims and accompanying drawings. It should be understood, however, that the following description, appended claims, drawings and the specific examples, while indicating preferred embodiments of the invention, are given by way of illustration only. Various changes and modifications within the spirit and scope of the disclosed invention will become readily apparent to those skilled in the art from reading the following.

BRIEF DESCRIPTION OF THE DRAWINGS

The following drawings depict certain embodiments of the invention. They are illustrative only and do not limit the invention otherwise disclosed herein.

FIG. 5. Av3hGK vector expression in primary rat hepatocytes. Primary rat hepatocytes (($5 \times 10^6$ cells) were infected with varying multiplicities of infection (MOI; 0–200 particles/cell) of Av3hGK, 200 particles/cell Av3Null or left untreated. Two days later, cells were harvested and lysates prepared for Western blot analysis with an antibody specific for GK (upper panel) or for GK enzymatic assays (lower panel). A dose dependent increase in both GK expression and activity was observed following vector administration. Note that the levels of GK expressed by Av3hGK are orders of magnitude higher than the endogenous rat GK (consistent with GK activity from the same samples). Alternatively, there may be a higher affinity of the antibody for the ectopic human GK protein than for the endogenous rat GK protein.

FIG. 7. C57BU6J mice from both HF and LF diets were treated with Av3hGK. Three weeks following the injection, blood samples were collected and the levels of plasma glucose, insulin, lactate, free fatty acids (FFA), triglycerides (TG), alanine transaminase (ALT) and insulin were measured. Av3hGK treatment in HF mice resulted in a lowering of fasting plasma glucose and insulin levels whereas lactate, FFA and TG levels were not affected. Blood chemistry in the LF group was not significantly affected except for plasma ALT levels which were elevated both in HF and LF groups.

FIG. 9. Av3hGKRP treatment does not result in excess fat accumulation in the livers of high-fat fed mice. C57BU6J mice maintained on a high-fat diet for 8 months were treated either with Av3hGKRP, Av3hGK, or Av3Null vector ($1.2 \times 10^{11}$ particles/animal) or with HBSS via tail vein injection (17 mice/group). Three weeks following the injections, these mice were sacrificed and liver samples were fixed in formaldehyde, paraffin embedded, sectioned and stained with hematoxylin and eosin. Representative photomicrographs from each treatment group are shown. Note the large increase in lipid vacuoles in the livers from Av3hGK treated mice, which are not seen in the Av3hGKRP treated mice.

DEFINITIONS

Figure 1:
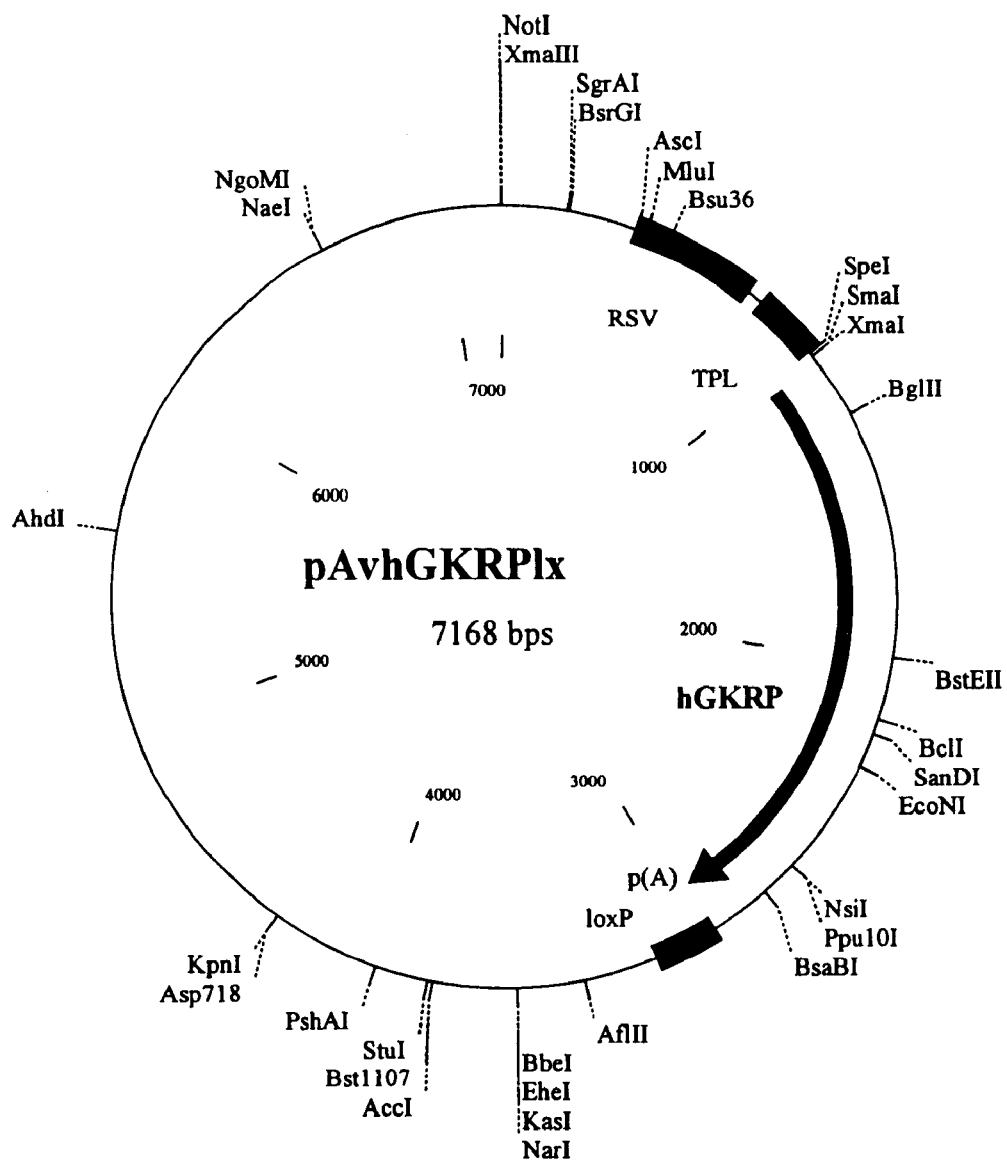
FIG. 1. Schematic diagram of the adenovirus shuttle plasmid, pAvhGKRPIx, used in construction of the Av3hGKRP (FIG. 3) adenoviral vector.

Unless otherwise specified herein, common definitions are intended by the words and terms used herein. As throughout this specification the singular is intended to include the plural and vice versa.

The term "one or more metabolism modifying proteins and peptides" as used herein includes, but is not limited to, UCP2 and UCP3, PPARα, OB-Rb, GLP-1 and GLP-1 analogs.

The term "protein product" as used herein includes natural, recombinant or synthetic proteins, biologically active protein variants (including insertion, substitution and deletion variants), and chemically modified derivatives thereof. Included are protein products that are substantially homologous to the human protein products.

The term "biologically active" as used herein means that the protein product demonstrates similar properties, but not necessarily all of the same properties, and not necessarily to the same degree, as the natural human protein products.

The term "substantially homologous" as used herein means a protein product having a degree of homology to the natural human protein product that is preferably in excess of 70%, most preferably in excess of 80%, and even more preferably in excess of 90% or 95%. The percentage of homology as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). Preferably the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the natural human protein product.

The term "polynucleotide sequence(s) encoding", include any polynucleotide sequence which encodes a respective protein product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The term "co-administration" as that term is used herein means that polynucleotide sequence(s) and the proteins they encode, and in appropriate cases compounds, are administered alone or in any combination to a subject, wherein the proteins are expressed 1) together as co-expression products from the same bicistronic or polycistronic vector or 2) separately in different vectors and/or compounds are administered either simultaneously, concurrently or sequentially with no specific time limits, wherein such administration provides therapeutically effective levels of the proteins and/or compounds in the subject at the same time. This term includes co-expression of two or more proteins simultaneously, concurrently or sequentially with no specific time limits from the same vector or different vectors.

The terms "infection", "transduction", and "transfection" are used interchangeably herein and mean introduction of a gene or polynucleotide sequence(s) into cells such that the encoded protein product is expressed.

The term "therapeutically effective amount" shall mean that amount of protein or compound that will elicit the biological or medical response of a tissue, system or animal (mammal) that is being sought by a researcher or clinician.

The terms "mammal", "mammalian organism", "subject" or "patient" are used interchangeably herein and include, but are not limited to, humans, dogs, cats, horses and cows. The preferred patients are humans.

The term "treat" or "treatment" encompasses the complete range of therapeutically positive effects associated with pharmaceutical medication including reduction of, alleviation of and relief from the symptoms or illness, which affect the organism. When treating diabetes, treatment includes the administration of a compound and/or the administration of a protein product by gene therapy to lower insulin levels, improve glucose tolerance and normalize the blood glucose level in the patient suffering from the hyperglycemic disorder. Normalize means to reduce the blood glucose level to an acceptable range, which means within 10, 8 or 5% of the normal average blood glucose level for the subject.

DESCRIPTION

In one aspect of the present invention there is provided a method of treating diabetes and diabetes-related conditions comprising administering to a subject in need thereof a therapeutically effective amount of a polynucleotide sequence encoding GKRP or GKRP in combination with a polynucleotide sequence encoding GK. In another aspect, the present invention provides a method of treating diabetes and diabetes-related conditions comprising administering to a subject in need thereof a therapeutically effective amount of a polynucleotide sequence encoding one or more metabolism modifying proteins and peptides in combination with a polynucleotide sequence encoding 1) GK or 2) GKRP or 3) GKRP in combination with GK. Preferred metabolism modifying proteins and peptides include UCP2 and UCP3, PPARα, OB-Rb, GLP-1 and GLP-1 analogs. Preferred examples of GLP-1 analogs include GLP-1-Gly8, Extendin-4, and the "Black Widow" chimeric GLP-1 analog (Holtz, G. G. and Habener, J. F. Comp. Biochem. Physiol. B. Biochem. Mol. Biol. 121:177–184, 1998; Drucker, D. J. Diabetes 47:159–169, 1998).

GK

The first stage of glycolysis is the preparation of glucose for the subsequent enzymatic steps by its phosphorylation to a negatively charged molecule at the expense of ATP. The phosphorylation of glucose at the 6 position by ATP to yield glucose 6-phosphate is catalyzed by GK. GK is present in the liver and pancreatic β-cells but is absent in tissues such as muscles and fat. It normally comes into play when the blood glucose concentration is temporarily high, as it is following a meal rich in sugar. However, this enzyme is deficient in some patients suffering from diabetes, in which there is a high blood-sugar concentration as a consequence of failure to secrete sufficient levels of the pancreatic hormone insulin. The GK protein product employed in the present invention can be any biologically active GK protein product. Preferably, GK is human GK. The amino acid sequence for human GK and methods for cloning are shown in Tanizawa, Y., et al. (Proc. Natl. Acad. Sci. USA 88:7294–7297, 1991). It is contemplated that proteins which are substantially homologous to the GK protein products described above and which retain GK biological activity may be employed in the methods of the present invention.

The polynucleotide sequences encoding GK protein products may be isolated or generated by any means known to those of skill in the art. In general, recombinant techniques involve isolating the polynucleotide sequence responsible for encoding GK, cloning the gene in suitable vectors and cell types, modifying the gene if necessary to encode a desired variant, and expressing the gene in order to produce the GK protein product. Alternatively, a polynucleotide sequence encoding a desired GK protein product may be chemically synthesized. Polynucleotide sequences encoding GK include any sequence which encodes a biologically active GK protein product. For example, the polynucleotide sequence encoding GK can be the same or substantially the same as the coding sequence of the endogenous GK coding sequence as long as it encodes a biologically active GK protein product. Similarly, the polynucleotide sequence can be the same or substantially the same as the GK gene of a non-human species as long as it encodes a biologically active GK protein product. Further, GK may be expressed using polynucleotide sequence(s) which differ in codon usage due to the degeneracies of the genetic code or allelic variations.

GK may be employed to treat diabetes and obesity as shown in example 1.

GKRP

Regulation of GK activity occurs via the binding of GKRP. Under low glucose concentrations, binding of GKRP to GK prevents GK translocation from the nucleus to the cytoplasm resulting in inhibition of GK activity. It has been proposed that GK is activated via disruption of the GK and GKRP interaction in response to hyperglycemia which allows for translocation of the enzymatically active GK from the nucleus to the cytoplasm.

Preferably, GKRP is human GKRP. The amino acid sequence for human GKRP and methods for cloning are shown in Warner, J. P., et al. (Mamm. Genome 6:532–536, 1995). It is contemplated that naturally occurring human GKRP and proteins which are substantially homologous thereto and which retain GKRP biological activity may be employed in the methods of the present invention.

The polynucleotide sequences encoding GKRP protein products may be isolated or generated by any means known to those skilled in the art. In general, recombinant techniques involve isolating the polynucleotide sequence(s) responsible for coding GKRP, cloning the gene in suitable vectors and cell types, modifying the gene if necessary to encode a desired variant, and expressing the gene in order to produce the GKRP protein product. Alternatively, a polynucleotide sequence encoding a desired GKRP protein product may be chemically synthesized. Polynucleotide sequence(s) encoding GKRP include any sequence which encodes a biologically active GKRP protein product. For example, the polynucleotide sequence encoding GKRP can be the same or substantially the same as the coding sequence of the endogenous GKRP coding sequence as long as it encodes a biologically active GKRP protein product. Similarly, the polynucleotide sequence can be the same or substantially the same as the GKRP gene of a non-human species as long as it encodes a biologically active GKRP protein product. Further, GKRP may be expressed using polynucleotide sequence(s) which differ in codon usage due to the degeneracies of the genetic code or allelic variations.

Figure 3:
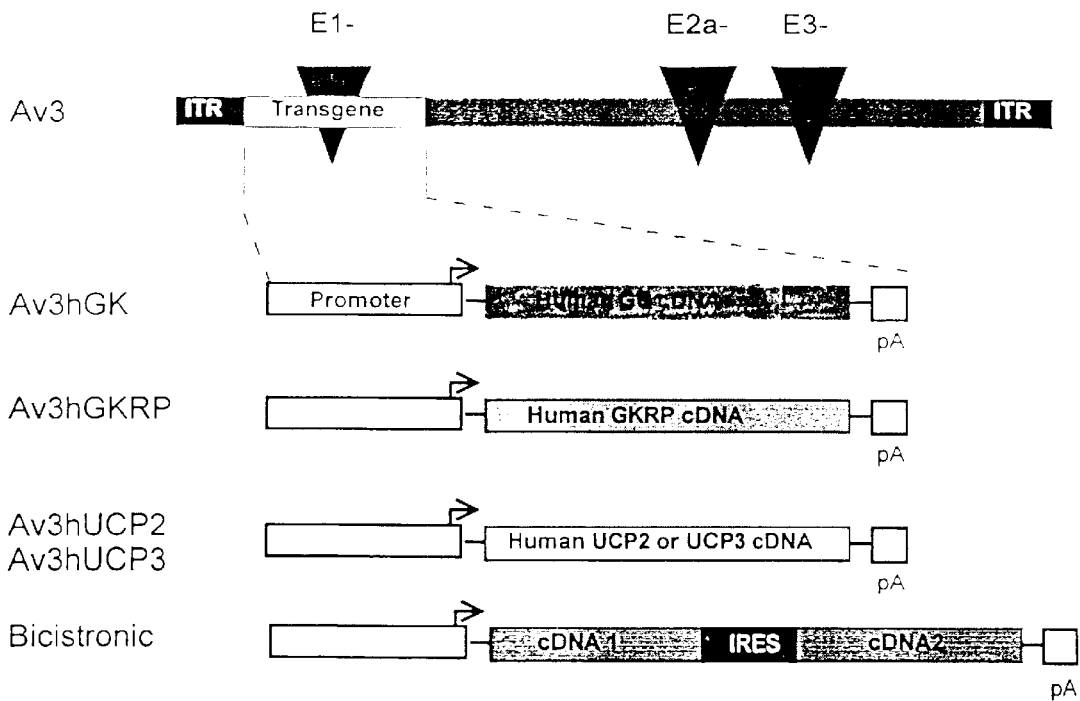
FIG. 3. Schematic diagram of third generation, E1/E2a/E3-deleted adenoviral vectors encoding single or multiple therapeutic genes.
Figure 4:
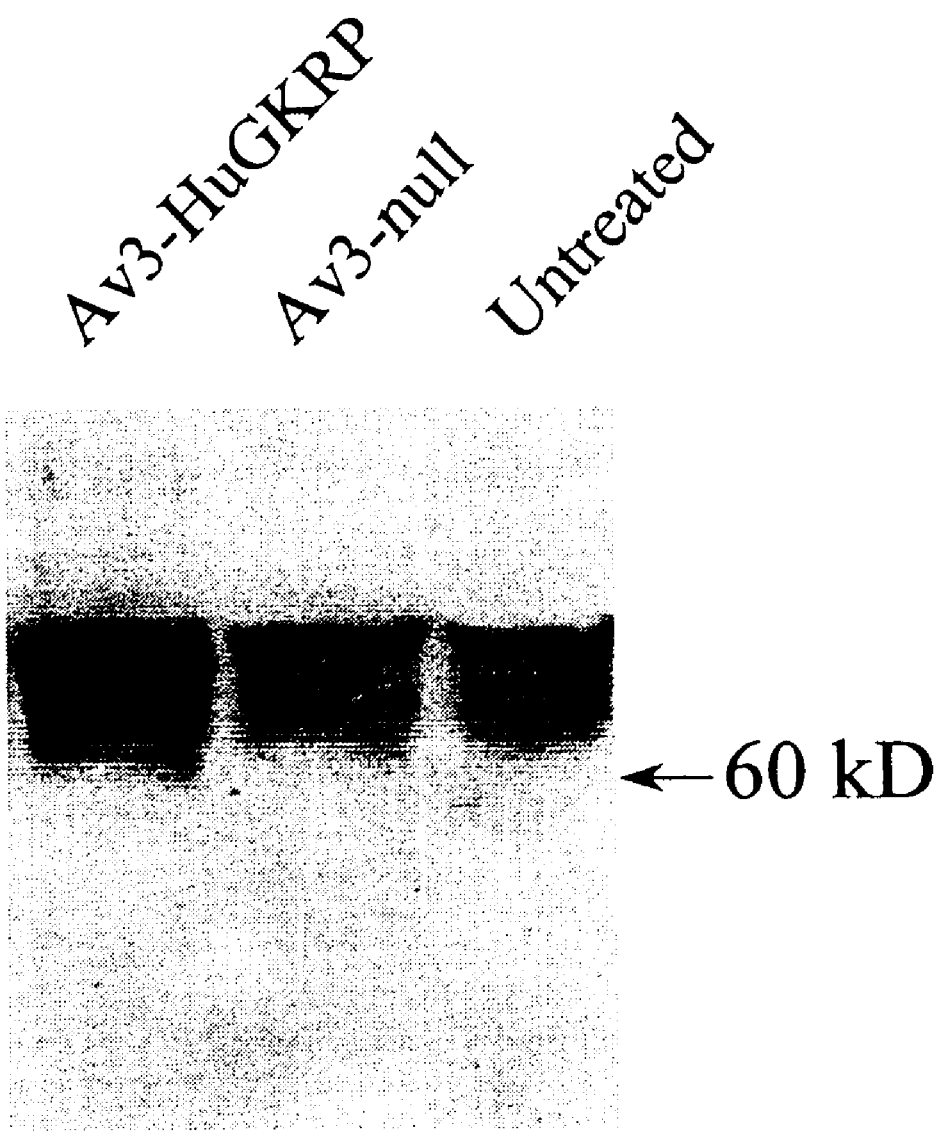
FIG. 4. Av3hGKRP vector expression in primary rat hepatocytes. Primary rat hepatocytes ($5 \times 10^6$ cells) were treated for 1 hour with 200 particles/cell of Av3hGKRP or Av3Null vectors or left untreated. Cells were harvested 2 days later and cellular extracts were prepared. Equal amounts of extract were loaded in each lane and proteins separated by 8% SDS-PAGE and then transferred to a PVDF membrane. Western blot analysis was performed using an antibody specific for GKRP and protein was detected by enhanced chemiluminescence (Amersham ECL). As shown, the Av3hGKRP vector was successfully transduced and GKRP expressed in hepatocytes.
Figure 11:
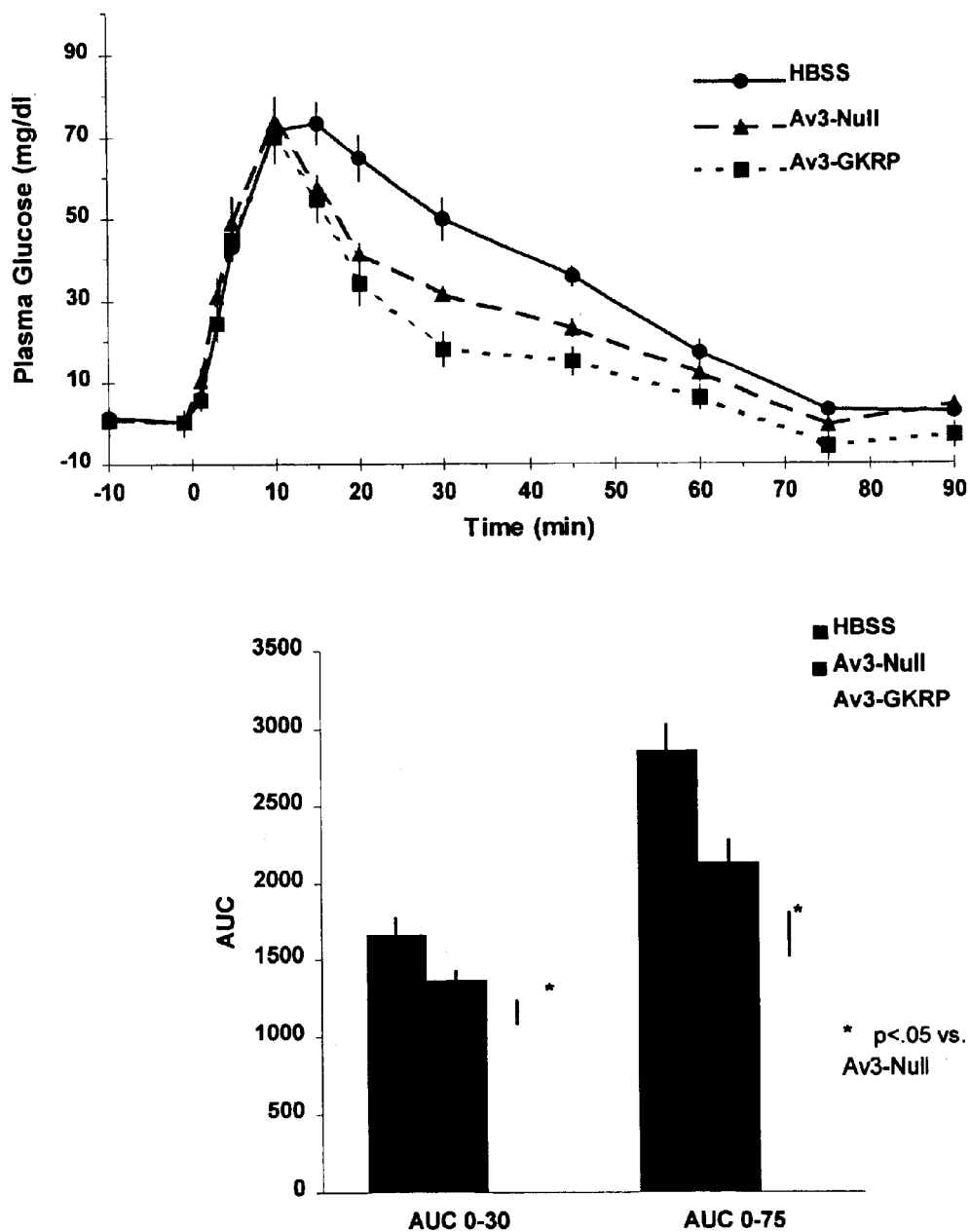
FIG. 11. Av3hGKRP improves glucose tolerance in high-fat fed rats. Sprague-Dawley rats maintained on a high-fat diet for 4 weeks were administered $1.15 \times 10^{12}$ particles/animals of Av3hGKRP or Av3Null vector or were treated with HBSS (n=8/group). Two weeks following treatment an OGTT was performed (see example 1). The upper panel represents the plasma glucose values (equalized to time 0) versus time. The lower panel represents the Area-Under-Curve from either time 0–30 min or 0–75 min. Data are the means ±SE. Av3hGKRP showed a statistically significant improvement in glucose tolerance compared to Av3Null ($p<0.05$; Students t test).
Figure 12:
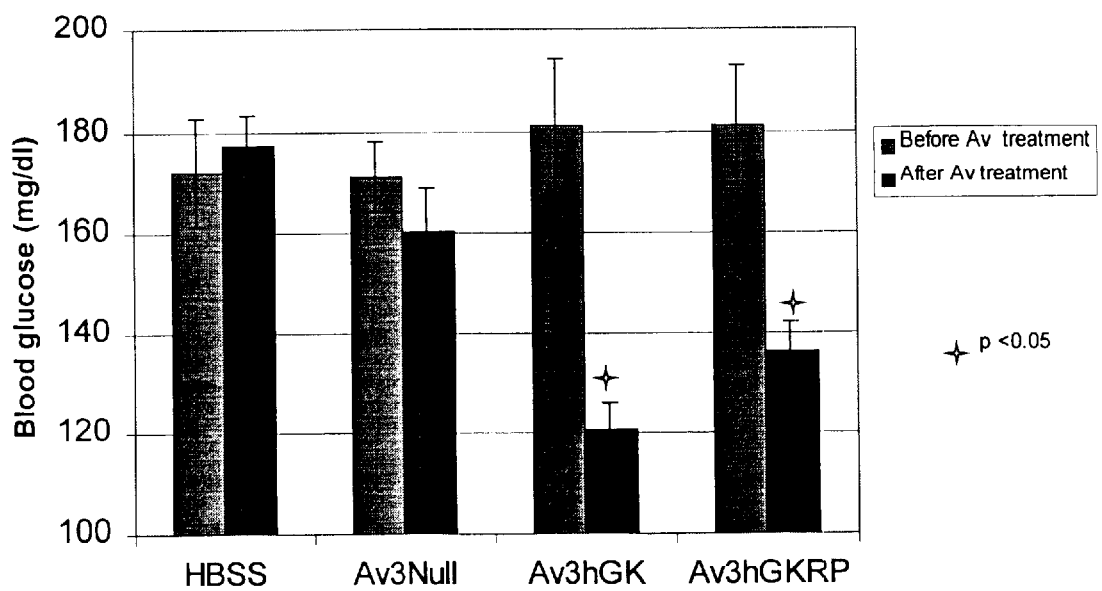
FIG. 12. Administration of Av3hGKRP significantly improves fasting blood glucose levels in high-fat fed mice. C57BL/6J mice were maintained on a high-fat diet for 8 months and divided into 4 age-matched groups. Each group (n=6–9) was treated either with the Av3Null, Av3hGK, orAv3hGKRP vector ($1.2 \times 10^{11}$ particles/animal) or with HBSS via tail vein injection. Blood samples (130 µl) were collected from overnight fasted animals before and at 3 weeks following vector administration. Blood glucose was analyzed using a hand held glucometer (Bayer Corp.) immediately after sample collection was complete. Data are the means ±SE. The statistical significance (*$p<0.05$) was determined by a paired Student's t test (comparing before and after vector treatment for each group).
Figure 13:
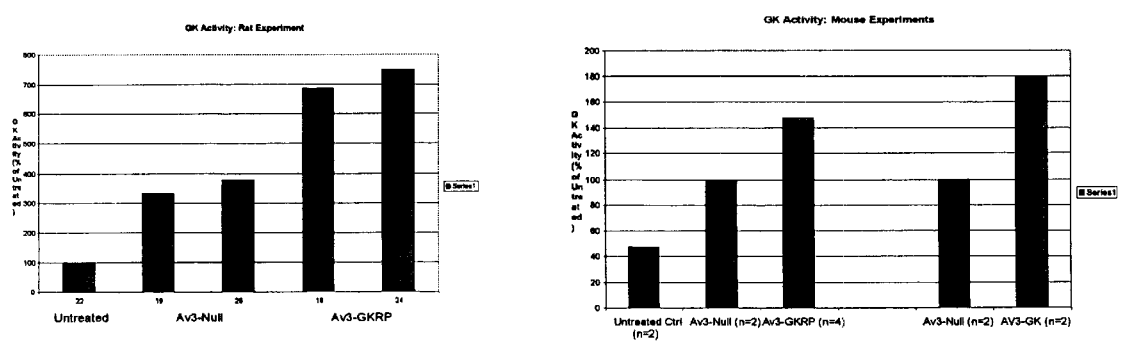
FIG. 13. Increased GK activity in rodents treated with Av3hGKRP. Individual rats (left panel) or groups of mice (right panel) were treated with the indicated vectors or left untreated. Liver samples were taken at 2 weeks and 3 weeks following the vector treatment in the rat and mouse studies, respectively. In each panel, GK activity relative to untreated or to Av3-Null treatment is shown. As indicated, administration of Av3hGKRP significantly increased GK activity as compared to control and Av3Null.

There is a high level of GKRP expression in cultured primary rat hepatocytes following treatment with Av3-GKRP vector (FIG. 4). Over-expression of GKRP by administration of a vector containing the polynucleotide sequence encoding the GKRP protein product, an E1/E2a/E3-deficient adenoviral vector encoding human GKRP, Av3hGKRP (FIG. 3), in high-fat (HF) fed rats improved glucose tolerance at 1 and 2 weeks following vector treatment (FIG. 11). Three weeks following this administration of Av3hGKRP to diabetic (high-fat diet induced) mice, an improvement in fasting blood glucose levels was observed (FIG. 12). The inventors have surprisingly found that the Av3hGKRP treated rats and mice also showed an increase in liver GK activity, suggesting that GKRP acts to stabilize GK (FIG. 13). These findings are unexpected since GKRP is thought to function as an inhibitor of GK.

Figure 8:
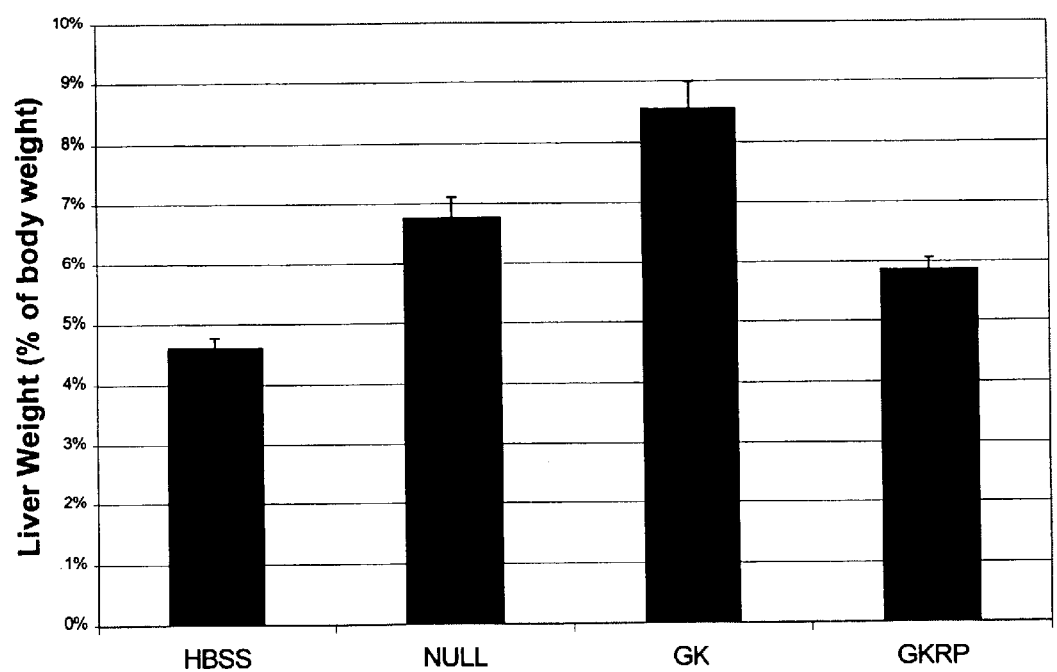
FIG. 8. Av3hGKRP treatment does not result in increased liver weight in high-fat fed mice. C57BU6J mice maintained on a HF diet for 8 months were treated with Av3hGKRP, Av3hGK, Av3Null ($1.2 \times 10^{11}$ particles/animal) or with Hanks' Balanced Salt Solution (HBSS) via tail vein injection (17 mice/group). Three weeks following the injections, these mice were weighed and sacrificed. The livers from the mice were carefully dissected free and weighed, and the liver weight as a percentage of whole body weight was plotted. Note that treatment with Av3hGK vector resulted in a sharp increase in liver weight, whereas liver weights of Av3hGKRP treated mice were even less than Av3Null treated mice. Data are the means ±SE.

Expression of GKRP has a further advantage over treatment of diabetes and diabetes-related diseases with GK. Treatment with GKRP does not result in increased liver weights or lipid accumulation in the liver as compared to treatment with GK, which increases lipid vacuole accumulation in the liver as shown in FIGS. 8 and 9. Hyperlipidemia following overexpression of GK in livers of low-fat fed rats has also been reported (O'Doherty, R. M. et al., Diabetes 48:2022–2027,1999). Thus GKRP expression may serve to avoid potentially toxic effects of increased GK activity.

Co-expression of GK and GKRP is required for optimal GK expression and function in the liver. This unexpected finding that over-expression of GKRP improved glucose tolerance and/or fasting blood glucose levels in HF fed rats (FIG. 11) and in diabetic mice (FIG. 12), by increasing GK protein and activity levels (FIG. 13), also provides evidence that the co-expression of GK and GKRP in hepatocytes, delivered by two vectors or a single, bicistronic vector (FIG. 3), would further increase GK activity levels. In addition, since unregulated overexpression of GK leads to increased liver weight and lipid accumulation in the liver (FIGS. 8 and 9), co-expression of GKRP with GK permits a means of regulating GK protein and activity levels.

Metabolism Modifying Proteins and Peptides

The metabolism modifying proteins and peptides of the present invention include, but are not limited to, UCP2 and UCP3, PPARα, OB-Rb, GLP-1 alone or in combination with a DPP-IV inhibitor and GLP-1 analogs. Preferred examples of GLP-1 analogs include GLP-1-Gly8, Extendin-4 and "Black Widow" chimeric GLP-1 analog.

The UCP proteins function to regulate the metabolism of lipids and function as mediators of thermogenesis (Samec, S. et al., FASEB J. 12:715–724, 1998). UCP3 is normally expressed in skeletal muscle (Langin, D. et al., Int. J. Obes. Relat. Metab. Disord. 23 (suppl 6):S64–67,1999), whereas UCP2 expression has been detected in liver (Chavin, K. D. et al., J. Biol. Chem. 274:5692–5700, 1999). The UCPs are mitochondrial inner-membrane transporter proteins that uncouple oxidative phosphorylation. This process results in the conversion of energy into heat rather than fat. Examples of DNA fragments containing the polynucleotide sequence encoding an uncoupling protein is set forth in SEQ ID NO's 1 and 3. The UCP protein they encode respectively are set forth in SEQ ID NO's 2 and 4.

Human PPARα controls the expression of fatty acid-metabolizing enzymes as shown in studies with PPARα knock out mice (Aoyama, T. et al., J. Biol. Chem. 273:5678–5684, 1998). These mice exhibit reduced hepatic fatty acid oxidation. In addition, Aoyama, T. et al. have shown that activation of PPARα (in wild-type mice but not in the knock out mice) with a PPARα ligand stimulates hepatic fatty acid oxidation. Moreover, Costet, P. et al. (J. Biol. Chem. 273:29577–29585, 1998) have shown that the PPARα knock-out mice have greatly increased hepatic triglyceride levels. Preferably, PPARα is human PPARα, deposited as Genbank Accession number L02932. The amino acid sequence of human PPARα and methods for cloning are shown in Sher, T. et al., (Biochemistry 32:5598–5604, 1993).

In addition, other authors (Zhou,Y. -T. et al., Proc. Natl. Acad. Sci. USA 95:8898–8903, 1998; Wang, M. -Y. et al., Proc. Natl. Acad. Sci. USA 95:714–718, 1998) have shown that in β-cells, PPARα activation can stimulate fatty acid oxidation and reduce the triglyceride content of islets. Zhou et al. expressed PPARα indirectly by over-expression of OB-Rb, which is the long form of the OB-R, containing a longer cytoplasmic domain required for activation of STAT proteins. The amino acid sequence of OB-Rb is shown in Ghilardi, N. et al., (Proc. Natl. Acad. Sci. USA 93:6231–6235, 1996). The mouse OB-Rb is deposited as Genbank Accession number U58861. Zhou et al. suggest that activation of OB-Rb with leptin results in PPARα expression which in turn causes the expression of fatty acid metabolic enzymes.

Representative PPARα ligands which are employed in the present invention include, but are not limited to, fibrates, for example, clofibrate, fenofibrate, bezafibrate, ciprofibrate, beclofibrate, etofibrate and gemfibrozil (Staels, B. and Auwerx, J., Atherosclerosis, 137: Suppl. S19–S23, 1998). Additional examples of PPARα ligands are KRP-297, SB 213068, L-796449, GW2433, GW 9578, GW 7845, JTT-501 and GI 262570 (Murakami, K. et al., Diabetes 47:1841–1847, 1998; Willson, T. M. et al. J. Med. Chem. 43:527–550, 2000).

The present invention includes all metabolism modifying protein products which are biologically active including those from species other than humans.

Polynucleotide sequences encoding metabolism modifying proteins include any sequence which encodes a biologically active metabolism modifying protein product. For example, the polynucleotide sequence(s) encoding metabolism modifying proteins can be the same or substantially the same as the coding sequence of the endogenous metabolism modifying protein coding sequence as long as it encodes a biologically active metabolism modifying protein product. Similarly, the polynucleotide sequence can be the same or substantially the same as the metabolism modifying proteins gene of a non-human species as long as it encodes a biologically active metabolism modifying proteins protein product. Further, metabolism modifying proteins may be expressed using polynucleotide sequence(s) which differ in codon usage due to the degeneracies of the genetic code or allelic variations.

Co-administration of UCP2 or UCP3 with GK, or in combination with GK and GKRP, may be employed to treat obesity by preventing the accumulation of hepatic fat by converting the excess energy as heat.

Another advantage of the present invention is that co-administration of GK, GKRP, UCP2 and UCP3, PPARα, OB-Rb and PPARα ligands, in any or all combinations, overcomes a limitation to the over-expression of GK in the liver. Over-expression of GK in normal and diabetic mice, results in an increased liver size and hepatic fat accumulation (FIGS. 8 and 9). Co-expression of UCP2 or UCP3 with GK counteracts the accumulation of hepatic fat and converts the excess energy as heat. This provides a gene therapy based treatment for obesity in conjunction with the treatment of diabetes. Further, co-administration of PPARα or OB-Rb with or without PPARα ligands also enhances liver fatty acid metabolism thereby preventing the buildup of excess lipids.

Co-administration of PPARα or OB-Rb with or without a PPARα ligand with GK alone, GKRP alone or with GK in combination with GKRP reduces hepatic triglyceride accumulation. The OB-Rb expression approach assumes that the same signaling pathway (i.e. leptin to OB-Rb to STAT3 to PPARα) can function in the liver as in β-cells. The liver contains primarily the short form of OB-R (Ghilardi, N. et al., Proc. Natl. Acad. Sci. USA 93:6231–6235,1996). An additional advantage of activation of PPARα is that apo A-I and HDL cholesterol levels also increase and fibrinogen levels decrease (Torra, I. P. et al., Curr. Opin. in Lipidol. 10:151–159,1999). Accordingly, co-administration of PPARα may be employed to increase apo A-I and HDL cholesterol levels and decrease fibrinogen levels.

Co-expression of GK alone, GKRP alone or GK and GKRP together with GLP-1 or an inhibitor of the enzyme that inactivates GLP-1, i.e. an inhibitor of dipeptidyl peptidase IV (DPP-IV), may be employed to treat diabetes and obesity. Alternatively. co-expression of GK alone, GKRP alone or GK/GKRP together with an analog of GLP-1 that is not susceptible to inactivation by DPP-IV such as GLP-1-Gly8 (Deacon, D. F. et al., Diabetologia 41:271–278, 1998), Exendin-4 (Drucker, D. J., Diabetes 47:159–169, 1998), or "Black Widow" chimeric GLP-1 analog (Holz, G. G. and Habener, J. F., Comp. Biochem. Physiol. B. Biochem. Mol. Biol. 121:177–184,1998) may be employed to treat diabetes and obesity.

Expression of GK, GKRP, UCPs, PPARα, OB-Rb, GLP-1, analogs of GLP-1 resistant to metabolic inactivation and/or other proteins or peptides using a lentiviral or a adeno-associated viral (MV) vector system overcomes a limitation of the adenoviral vector system. For the treatment of a chronic disease such as diabetes, a vector system that can mediate long-term or life-long expression is warranted. Lentiviral and MV vectors integrate into the host chromosomal DNA, and therefore, provide long-term therapeutic gene expression (Kalpana, G. V., Semin. Liver Dis. 19:27–37,1999; Muzyczka, N., Curr. Top. Microbiol. Immunol. 158(97):97–129, 1992).

Administration of GK alone, GKRP alone or GK and GKRP together with other metabolism modifying proteins such as PPARα and the leptin receptor, OB-Rb alone, or in combination with PPARα ligands may be employed to treat diabetes, obesity and for preventing liver triglyceride accumulation.

In accordance with another aspect of the present invention, additional compounds may be co-administered with the combinations of proteins and peptides described above. The compounds include, but are not limited to, PPARα ligands and DPP-IV inhibitors. Preferred examples of DPP-IV inhibitors include N-(N'-substituted glycyl)-2-cyanopyrrolidines as disclosed in U.S. Pat. No. 6,011,155 issued Jan. 4, 2000. Preferred examples of PPARα ligands include clofibrate, fenofibrate, bezafibrate, ciprofibrate, beclofibrate, etofibrate and gemfibrozil (Staels, B. and Auwerx, J., Atherosclerosis, 137 Suppl.:S19–S23,1998). Additional examples of PPARα ligands include KRP-297 (Murakami, K. et al., Diabetes 47:1841–1847,1998), DRF-2519 (Chakrabarti, R. K. et al., Keystone Symposia; The PPARs: Transcriptional Links to Obesity, Diabetes and Cardiovascular Disease, Abstract # 103, 1999), GW2331 (Kliewer, S. A. et al., PNAS, USA 94:4318–23, 1997), JTT-501, GW 2433, SB 213068, GI 262570, GW 7845 and L-796449 (Willson, T.M. et al., J. Med. Chem. 43:527–550, 2000).

Administration

GK, GKRP and the one or more metabolism modifying proteins and peptides may be administered by gene therapy. In this aspect of the present invention there are provided vectors comprising a polynucleotide sequence encoding 1) GK 2) GKRP or 3) GKRP in combination with GK. In another embodiment of this aspect of the invention there are provided vectors comprising a polynucleotide sequence(s) encoding one or more metabolism modifying proteins and peptides in combination with 1) GK or 2) GKRP or 3) GKRP in combination with GK.

Genetic delivery vehicles for the polynucleotide sequences encoding a protein product(s) of the present invention, includes any vector suitable for promoting expression of the protein product(s). For example, a polynucleotide sequence(s) encoding a protein product of the present invention may be contained in adeno-associated virus vectors which are disclosed in U.S. Pat. Nos. 5,139, 941, 5,436,146, and 5,622,856 an attenuated or gutless adenoviral vector, see Morsy, M. A. and Caskey, C. T., (Mol. Med. Today 5:18–24, 1999 and U.S. Pat. No. 5,935,935), lentiviral vectors which are disclosed in U.S. Pat. Nos. 5,665,577, 5,994,136, and 6,013,516 or synthetic (non-viral) vectors which are disclosed in U.S. Pat. Nos. 4,394,448, and 5,676,954. Alternative viral vectors include, but are not limited to, retroviral vectors which are disclosed in U.S. Pat. Nos. 5,672,510, 5,707,865, and 5,817,491, herpes virus vectors which are disclosed in U.S. Pat. No. 5,288,641, and sindbis virus vectors and papilloma virus vectors as disclosed in EP 820 773. The vectors may be either monocistronic, bicistronic or multicistronic. Synthetic vectors are preferred, MV vectors are even more preferred and the lentiviral vector system is most preferred.

An adenoviral vector may include essentially the complete adenoviral genome (Shenk, et al., Curr. Top. Microbiol. Immunol., 111:1–39, 1984). Alternatively, the adenoviral vector may be a modified adenoviral vector in which at least a portion of the adenoviral genome has been deleted. Adenoviral vectors may be produced according to He, et al. (PNAS 95:2590–2514, 1998; Chartier, et al., J. Virol. 70:48054810, 1996 and Hitt, et al., Methods in Molecular Genetics, 7:13–30, 1995). Methods of transferring genes into cells using adenoviral vectors has been described in PCT/US95/15947. A number of adenoviral vectors have been developed for the transduction of genes into cells (Berkner, et al., BioTechniques 6:616–629, 1988). Constitutive high level expression of the transduced gene products has been achieved. These vectors have the inherent advantage over the retroviral vectors in not requiring replicating cells for infection, making them suitable vectors for somatic gene therapy (Mulligan, R. C., Science 260:926–932, 1993).

The feasibility for transducing genes associated with glucose metabolism, using adenovirus-mediated transfer in primary rat hepatocytes and myoblast in culture, has been described (Baque, et al., Biochem. J. 304 (Pt 3):1009–1014, 1994; Gomez-Foix, et al., J. Biol. Chem. 267:25129–25134, 1992).

Preferably the adenoviral vector is an Av3 vector as disclosed in Gorziglia, M. I., et al. (J. Virol. 6:41734178, 1996). Av3 vectors have been constructed and used to transduce primary human hepatocytes as disclosed in Connelly, S., et al., Blood 91:3273–3281, 1998; Connelly, S., et al., Thromb. Haemost. 81:234–239, 1999; Andrews, J. L., et al., Haemophilia 5:160–168, 1999; Gallo-Penn, A. M., Hum. Gene Ther. 10:1791–1802, 1999; and Brann, T., et al., Hum. Gene Ther. 10:2999–3011, 1999.

Av3hGKRP (or Av3hGK) is a third generation adenoviral vector containing human liver GKRP (or GK) cDNA under the control of the RSV promoter. The vector backbone was derived from adenoviral serotype 5 (Ad5) and is devoid of E1, E2a and E3 regions (Gorziglia et al, 1996). For details of vector construction see example 1. One mode of administration would be via i.v. administration to a diabetic patient through a peripheral vein. The vector would transduce hepatocytes in the liver and express the transgene (in this case, GKRP (or GK)).

Retroviral vector production and use are also known per se. See for example, U.S. Pat. No. 5,910,434, Veres, et al., J. Virol., Vol. 72:1894–1901, 1998; Agarwal, et al., J. Virol., Vol. 72:3720–3728, 1998; Forestell, et al., Gene Therapy, 4:600–610, 1997; Plavec, et al., Gene Therapy, 4:128–139, 1997; Forestell, et al., Gene Therapy, 2:723–730, 1995; and Rigg, et al., J. Virol., 218:290–295, 1996. The genome of recombinant retroviral vector is comprised of long terminal repeat (LTR) sequences at both ends which serve as a viral promoter/enhancer and a transcription initiation site and a Psi site which serves as a virion packaging signal and a selectable marker gene. An example of such vector is pZIP NeoSV (Cepko, et al., Cell 53:103–1062, 1984). The polynucleotide sequence(s) disclosed herein can be cloned into a suitable cloning site in the retroviral genome. Expression is under the transcriptional control of the retroviral LTR. Tissue selectivity is determined by both the origin of the viral genome (e.g., sarcoma virus, leukemia virus, or mammary tumor virus) and the cell line used to package the virus.

Recombinant retroviruses capable of transducing the polynucleotide sequences of the present invention are produced by transfecting the retroviral genome(s) into a suitable (helper-virus free) amphotropic packaging cell line. The transfected virus packaging cell line will package and produce recombinant retroviruses, shedding them into the tissue culture media. The retroviruses are harvested and recovered from the culture media by centrifugation.

Adeno-associated virus can also be used as a vector for transducing an expression cassette. As with adenoviruses, AAV is capable of infecting post-mitotic cells, thereby, making it a suitable vector for delivery of genes to somatic cells.

The MV genome contains two genes, rep and cap, and inverted terminal repeats (ITR) sequences (Hermonat, et al., J. Virol. 51:329–339, 1984). Recombinant MV vectors are constructed by replacing the rep gene, the cap gene, or both with a gene expression cassette (Hermonat, et al., Proc. Nati. Acad. Sci. USA 81:6466–6470, 1984). The sole sequence needed for MV vector integration is the terminal 145 base ITR (Muzyczka, Curr. Top. Microbiol. Immunol. 158(97):97–129, 1992). Such vectors are available in the plasmid form (Tratschin, et al., Mol. Cell Biol. 5:3251–3260, 1985; Lebkowski, et al., Mol. Cell Biol. 8:3988–3996, 1988; and McLaughlin, et al., J. Virol. 62:1963–1973, 1988). The recombinant MV genomes can be packaged into MV particles by co-transfection of the vector plasmid and a second packaging plasmid carrying the rep and cap genes into an adenovirus-infected cell. Such particles have been shown to efficiently transduce heterologous genes into a number of mammalian cell lines (Tratschin, et al., Mol. Cell Biol. 5:3251–3260, 1985; Lebkowski, et al., Mol. Cell Biol. 8:3988–3996, 1988; McLaughlin, et al., J. Virol. 62:1963–1973, 1988; Flotte, et al., Am. J. Respir. Cell. Mol. Biol. 7:349–356, 1992)).

Sindbis virus-based vectors are intended as self-amplifying systems to enhance expression of exogenous genes in mammalian cells (Herweijer, et al., Human Gene Therapy 6:1161–1167, 1995). Recombinant sindbis virus is generated by placing the entire genome under the control of the bacteriophage T7 or SP6 promoters to enable transcription of the (+) strand RNA in vitro (Herweijer, et al., Human Gene Therapy 6:1161–1167, 1995. The resultant RNA genomes are then used to transfect target cells (Xiong, et al., Science 243:1188–1191, 1989). Infectious viruses are produced by infecting with a helper virus (Bredenbeek, et al., J. Virol. 67:6439–6446, 1993). Modifications of this design using the Rous sarcoma virus LTR to direct the transcription of the non-structural genes have been described (Herweijer, et al., Human Gene Therapy 6:1161–1167, 1995).

To generate a recombinant Sindbis virus vector, the luciferase gene cloned into the unique XbaI site in the vector pSin-Lux (Herweijer, et al., Human Gene Therapy 6:1161–1167, 1995) is replaced by an expression cassette encoding a protein product of the present invention upon appropriate restriction endonuclease modifications. See Sambrook, et al., Molecular Cloning—A Laboratory Manual (Cold Spring Harbor Laboratory, 1989). The above vectors are disclosed in EP 820 773.

Examples of cells suitable for genetic modification to incorporate a polynucleotide sequence encoding a protein product of the present invention includes hepatocytes, myocytes, myoblasts, stem cells, fibroblasts and endothelial cells.

In accordance with yet another aspect of the present invention there is provided a method of expressing 1) GKRP or 2) GKRP in combination with GK comprising transducing cells in vivo with a vector comprising a polynucleotide sequence encoding 1) GKRP or 2) GKRP in combination with GK, such that the cells are modified to produce the respective proteins and peptides.

In accordance with still another aspect of the present invention there is provided a method of expressing one or more metabolism modifying proteins and peptides in combination with 1) GK or 2) GKRP or 3) GKRP in combination with GK comprising transducing cells in vivo with a vector comprising a polynucleotide sequence encoding one or more modifying proteins in combination with a polynucleotide encoding 1) GK or 2) GKRP or 3) GKRP in combination with GK, such that the cells are modified to produce the respective proteins and peptides.

A preferred method of administration is by gene therapy. Gene therapy is generally disclosed in U.S. Pat. No. 5,399,346. Gene therapy means genetic modification of cells by the introduction of exogenous DNA or RNA into these cells for the purpose of expressing or replicating one or more peptides, polypeptides, proteins, oligonucleotides, or polynucleotides in vivo for the treatment or prevention of disease or deficiency in humans or animals.

In one embodiment the Av3 vector is introduced via i.v. administration to a diabetic patient through a peripheral vein. The vector transduces hepatocytes in the liver and expresses the transgene (i.e. GKRP or GK) to produce protein product(s).

The pharmaceutical compositions comprise vectors comprising a polynucleotide sequence encoding 1) GKRP or 2) GKRP in combination with GK and a pharmaceutically acceptable carrier suitable for administration to a subject. In accordance with this aspect of the invention there is provided a pharmaceutical composition comprising vectors comprising a polynucleotide sequence encoding one or more metabolism modifying proteins and peptides in combination with 1) GK or 2) GKRP or 3) GKRP in combination with GK and a pharmaceutically acceptable carrier suitable for administration to a subject.

Any suitable route of administration may be employed for providing a subject with pharmaceutical compositions of the present invention. For example, parenteral (subcutaneous, intramuscular, intravenous, transdermal) and like forms of administration may be employed. Dosage formulations include injections, implants, or other known and effective gene therapy delivery methods.

For parenteral compositions, the vectors will be stored in a buffer containing 200 mM Tris (pH 8.0), 50 mM HEPES, 10% glycerol at −70° C. until use. Prior to the delivery, the vector will be thawed on ice and diluted to the appropriate volume in saline. The carrier will usually comprise sterile water, at least in large part, though other ingredients, to aid solubility for example, may be included. Injectable solutions, for example, may be prepared in which the carrier comprises polyethylene glycol (PEG), saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect on the skin. It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient (s) calculated to produce the desired therapeutic effect in association with the required pharmaceutical carrier.

The PPARα ligands and DPP-IV inhibitors are administered using convenient administration techniques including intravenous, intradermal, intramuscular, subcutaneous, and oral. Oral dosing is preferred. For oral dosing, the compounds are combined with pharmaceutically acceptable carriers and formulated into tablets or capsules and the like. The therapeutically effective dosage of the pharmaceutical compositions of this invention will vary with the severity of the condition to be treated, the route of administration and the combinations administered. The dose, and perhaps the dose frequency, will also vary according to the age, body weight, and response of the individual patient. In general, administration of the pharmaceutical compositions comprising the vectors will be administered approximately no more frequently than once a month. In one embodiment, the vector particles may be administered in an amount of from about 1 to about $10^{16}$ particles/kg, preferably from about $10^5$ to about $10^{14}$ particles/kg, and more preferably from about $10^8$ to about $10^{13}$ particles/kg, and most preferably from about $10^{11}$ to $10^{12}$ particles/kg. This administration will provide a therapeutically effective amount of the protein products for the conditions described herein. It may be necessary to use dosages outside these ranges in some cases as will be apparent to those skilled in the art. Further, it is noted that the clinician or treating physician will know how and when to interrupt, adjust, or terminate therapy in conjunction with individual patient response. The term "therapeutically effective amount" is encompassed by the above-described dosage amounts and dose frequency schedule.

The diabetes and diabetes-related conditions which are treated by the above-described methods include, but are not limited to, diabetes characterized by the presence of elevated blood glucose levels, for example, hyperglycemic disorders such as diabetes mellitus, including both type 1, type 2 and gestational diabetes as well as other hyperglycemic related disorders such as obesity, increased cholesterol, kidney related disorders, cardiovascular disorders and the like. The above-described methods may be employed to lower insulin levels, improve glucose tolerance, increase hepatic glucose utilization, normalize blood glucose levels, increase apo A-1 and HDL levels, decrease fibrinogen levels, stimulate hepatic fatty acid oxidation, reduce hepatic triglyceride accumulation and normalize glucose tolerance.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Example 1

Improvement of Fasting Blood Glucose Levels and/ or Glucose Tolerance by Administration of GKRP The 1.9 kb full-length cDNA encoding human liver GKRP (Warner et al., Mamm. Genome 6:532–536, 1995) was PCR amplified from human liver Quick-Clone cDNA (Clontech, Palo Alto, Calif.) with primers containing EcoRI and SalI cleavage sites ((upstream primer 5'-GAATTCATGCCAGGCACAAAACGGTTT-3' (SEQ ID No. 5) and downstream primer 5'-GTCGACTCACTGAACGTCAGG CTCTAG-3'(SEQ ID No. 6)). PCR was performed with 1 ng of liver cDNA using the following conditions: 95° C. for 5 min; 30 cycles of 94° C. for 30 sec, 60° C. for 1 min, 72° C. for 2 min. The resulting PCR product was purified from an agarose gel using the QIAEX II kit (Qiagen, Valencia, Calif.) and then ligated into the TA-cloning vector, pCR2.1 (Invitrogen, Carlsbad, Calif.). The cDNA insert sequence was verified using ABI prism dye-terminator cycle sequencing on a Model 377 DNA Sequencer (PE Biosystems, Foster City, Calif.). This plasmid was digested with EcoRI and SalI, and the 1.9 kb GKRP cDNA fragment was blunt-ended with T4 DNA polymerase (Klenow fragment), gel purified and ligated into the EcoRV site of the adenoviral shuttle vector pAvS6a to form pAvS6a-hGKRP. Finally, a 2 kb BamHI fragment from pAvS6a-hGKRP was subcloned into the BamHI site of pAvS6alx (shuttle vector containing lox site, Genetic Therapy, Inc., Gaithersburg, Md.) to generate pAvh-GKRPIx (FIG. 1). The GKRP expression cassette included a constitutive RSV promoter, a 198 bp fragment containing the adeno-tripartite leader sequence, lox recombination sequence, and an SV40 early polyadenylation signal.

Figure 2:
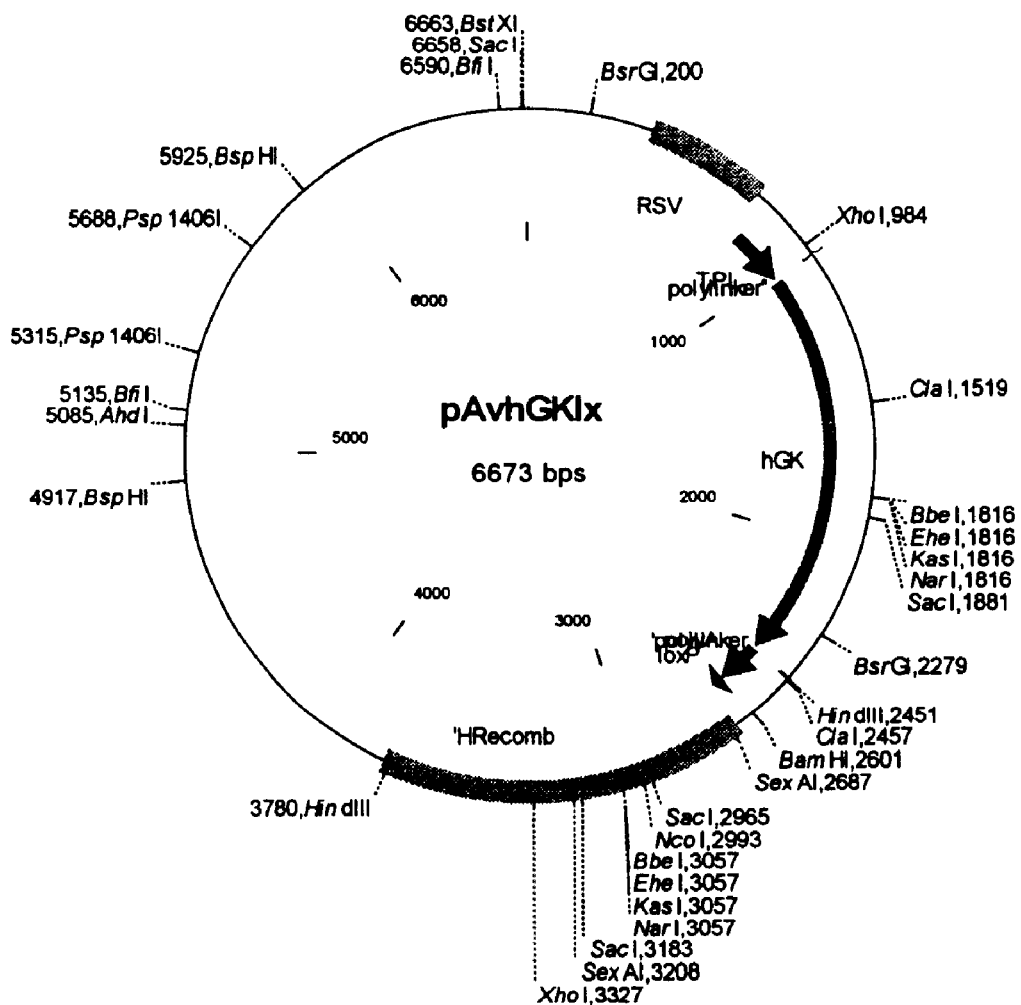
FIG. 2. Schematic diagram of the adenovirus shuttle plasmid, pAvhGKIx, used in construction of the Av3hGK (FIG. 3) adenoviral vector.

The 1.4 kb full-length cDNA encoding human liver GK (Tanizawa et al., Proc. Natl. Acad. Sci. USA 88:7294–7297, 1991) was PCR amplified from a human liver cDNA library (Clontech, Palo Alto, Calif.). PCR was carried out using 1 ng of the library and primers containing EcoRI and SalI cleavage sites ((upstream primer 5'-GAATTCATGGCGATG GATGTCACAAGG-3' (SEQ ID No. 7) and downstream primer 5'-GTCGACTCACTGGCCCAGCATACAGG-3' (SEQ ID No. 8)), using Clontech's Advantage-GC cDNA PCR kit according to the manufacturer's instructions. After heating the reaction for 1 min. at 94° C., PCR was performed using 30 sec. at 94° C. followed by 3 min. at 68° C. for 35 cycles with a final extension for 3 min. at 68° C. The resulting PCR product was purified from an agarose gel using the QIAEX II kit (Qiagen, Valencia, Calif.), digested with EcoRI-SalI and ligated to EcoRI-SalI cleaved pGEX-4T-1 (Amersham Pharmacia Biotech, Piscataway, N.J.) to generate pGEX-4T-1-hGK. The CDNA insert was verified by DNA sequencing. This plasmid was digested with SalI, klenow-filled and then digested with EcoRI. A double-stranded EcoRI adapter containing an overhang complementary to the SpeI site of the vector pAvS6a ((5'-CTAGCCACC CACCCC-3' (SEQ ID No, 9) and 5'-AATGGGGTGGGTGG-3'(SEQ ID No. 10)) was ligated to the EcoRI site of the GK cDNA fragment. The resulting fragment was ligated into pAvs6a digested with SpeI and EcoRV to generate pAvhGK. The BamHI-NcoI fragment (392 bp) from pAvH8101 (Genetic Therapy, Inc.) containing a lox site was inserted into the BamHI-NcoI sites of pAvhGK (6281 bp) to generate pAvhGKIx (FIG. 2).

The recombinant adenovirus encoding human GKRP (Av3hGKRP) or GK (Av3hGK) were constructed by a rapid vector generation protocol using Cre recombinase-mediated recombination of two lox-site containing plasmids, pSQ3 (containing the right hand portion of the adenoviral vector genome), and the adenoviral shuttle plasmid pAvhGKRPIx (containing the left end of the viral genome and the hGKRP expression cassette) or pAvhGKIx. The pSQ3 (digested with ClaI), pAvhGKRPIx or pAvhGKIx (linearized with NotI), and the Cre-encoding plasmid, pC-Cre3.1, were cotransfected using $CaPO_4$ (Promega's Profection kit) into S8 cells (A549 cells stably transfected with E1/E2a regions under dexamethasone inducible promoters (Gorziglia et al., J. Virol. 6:41734178, 1996). Following treatment with dexamethasone (0.33 $\mu$M), the plasmids were joined by Cre-mediated recombination, generating the adenovirus encoding GKRP (Av3hGKRP) or GK (Av3hGK) (FIG. 3). The Av3Null vector was generated in a similar manner, but lacks a transgene.

To amplify the virus, the cells were harvested a week after transfection and passaged until a cytopathic effect (CPE) was observed. For the passage, cells were freeze (dry ice)/thawed (37° C.) 5 times to obtain a CVL (crude viral lysate), which was centrifuged to remove the cell debris and then used to infect fresh S8 cells. Cells were harvested when CPE was observed, typically after one week. DNA was isolated from the CVL and the appropriate cre-lox mediated recombination event was confirmed by restriction digest. For purification of the vector, cell pellets were freeze/thawed 5 times (as above) and the cell debris was pelleted by centrifugation at 3,000 rpm for 10 min at 4° C. The supernatant was loaded on a discontinuous Cesium Chloride gradient (1.25 g/ml CsCl and 1.4 g/ml CsCl) and centrifuged for 1 hr at 28,000 rpm (in a SW28 swing bucket rotor). The bottom viral band was pulled from the gradient and centrifuged on a CsCl continuous gradient (1.33 g/ml CsCl) for overnight at 60,000 rpm (in an NVT-65 rotor). The purified viral band was pulled from the gradient, glycerol was added to a final concentration of 10% and the mixture was dialyzed in 200 mM Tris pH 8.0, 50 mM Hepes, 10% glycerol for $\geq$16 hr at 4° C. The concentration of vector was determined by spectrophotometric analysis (Mittereder et al., J. Virol. 70:7498–7509, 1996) and the vector was then was aliquoted and stored at $-70$° C.

Av3hGKRP and Av3hGK vector expression was examined in primary rat hepatocytes. Livers from anaesthetized Male Sprague-Dawley rats (approximately 280 g) were perfused with collagenase and hepatocytes isolated according to the procedure of Berry and Friend (J. Cell Biol. 43, 506–520, 1969). Hepatocytes were seeded in 10 cm plates ($5\times10^6$ cells/plate), and cultured at 37° C. (5% $CO_2$, 95% air) for 5 hr to allow for cell attachment. The cells were then treated for 1 hour with 200 particles of vector (Av3hGKRP or Av3Null)/cell, varying multiplicities of infection (MOI from 0–200 particles/cell) of Av3hGK or left untreated. Two days following treatment, cell extracts were prepared and Western blot analysis was performed using an antibody specific for GKRP or GK (Santa Cruz Biotechnology, Inc.). The biological activity of the expressed GK protein was confirmed by measuring GK activity using a method essentially as described by Hariharan et al. (Diabetes 46:11–16, 1997), except the assay buffer contained 100 mM Tris-HCl, pH 7.4, 100 mM KCl, 6 mM $MgCl_2$, 1 mM DTT, 5 mM ATP, 1 mM thioNAD, 30 units/ml glucose-6-phosphate dehydrogenase and 0.5 or 100 mM glucose. GK activity was estimated as the differences in activity when samples were assayed at 100 mM (GK plus hexokinase activity) and 0.5 mM glucose (hexokinase activity). Av3hGKRP was successfully transduced and overexpressed in hepatocytes, whereas only the endogenous rat GKRP protein was detectable in Av3Null or untreated cells (FIG. 4). Treatment with Av3hGK resulted in a dose-dependent increase in GK expression and activity levels (FIG. 5).

Male Sprague-Dawley rats were obtained from Harlan (Indianapolis, Ind.) and were maintained on a high-fat diet (57% fat calories, 19% protein calories, and 24% carbohydrate calories—Purina Test Diet) for one month. All rats were housed in individual cages in a pathogen free barrier facility and were maintained in an environmentally controlled animal facility (12 hr light/dark cycle) and were allowed free access to water and food.

Male C57BL/6J mice and ob/ob mice (34 weeks of age) were obtained from Jackson Laboratories (Bar Harbour, Me.). The C57BL/6J mice were maintained on either a normal chow diet for 8–10 weeks or on a high-fat diet (HF; 58% fat calories (lard), 25.6% carbohydrate calories—maltose dextrin plus sucrose, and 16.4% protein calories) (Surwit et al., Proc. Natl. Acad. Sci. USA, 95:40614065, 1998) for 4–8 months to induce diabetes. The HF diet also contained the required amounts of minerals and vitamins and were obtained from Research Diet, Inc. (New Brunswick, N.J., HF diet cat. #D12309R). The ob/ob mice were maintained on a normal chow diet for 2 months. All mice were housed 5 per cage in a pathogen free barrier facility and were maintained on a 12 hr light/dark cycle.

For viral dosing of rats, before each study, jugular venous catheters were surgically implanted into animals using established procedures (Giddings et al., Am. J. Physiol. 265: E259–266,1993). The subsequent day, rats were administered either $1.15 \times 10^{12}$ viral particles/animal of Av3hGKRP or Av3Null in a final volume of 750 μl sterile HBSS or were treated with HBSS alone (n=8–10 per group). Vector was administered by injecting it into the catheter tubing using a 1 ml syringe (Becton Dickinson, Santy, Utah). Daily body weights and bi-weekly food consumption were measured. Oral glucose tolerance tests (OGTT) were performed at 1, 2, and 3 weeks following viral administration. Body weights of overnight fasted rats were recorded and 500 μl of blood was collected (via jugular catheter) in EDTA/aprotinin tubes. A glucose bolus (1 g/kg body weight) was then administered by an oral gavage (at time 0 min). Blood (500 μl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

For viral dosing of mice, male C57BL/6J mice maintained on normal chow until 9 weeks of age or on a HF diet for 6–8 months were administered recombinant adenoviruses via tail vein injection using a 0.5 ml tuberculin syringe (Becton Dickinson, Sandy, Utah) at doses of $0.6$–$1.2 \times 10^{11}$ and $1.0$–$1.2 \times 10^{11}$ viral particles/animal, respectively, in a final volume of 100 μl sterile HBSS. Four groups of animals (n=5–15/group) were treated with either Av3hGKRP, Av3hGK, Av3Null or HBSS (n=5–15/group). OGTTs were performed at 1 week before or at 1, 2 and 3 weeks following viral administration. Body weights of overnight fasted mice were recorded and 50 μl of blood was collected via tail nick bleeds (or retro-orbital bleeds) in Heparin Fluoride and Lithium coated tubes. A glucose bolus (1 g/kg body weight) was then administered by oral gavage (at time 0 min). Blood (50 μl) was collected exactly at time 30 and 120 min. An OGTT was performed on ob/ob mice (maintained on normal chow) after 2 months. A month later, these mice were divided into 3 groups and were treated with $1.2 \times 10^{11}$ particles/animal of Av3hGK, Av3Null or HBSS via tail vein injection. Two weeks later, an OGTT was performed as described above.

All blood samples (rat and mice) were kept on ice and then centrifuged to isolate the plasma supernatant, from which glucose levels were determined using a YSI 2700-D Biochem Glucometer (YSI Inc.). Plasma immunoreactive insulin (IRI) concentrations were assayed either by using a double antibody RIA method with a specific anti-rat insulin antibody from Linco Research (St. Louis, Mo.) or by using a rat insulin ELISA kit (Crystal Chem) with mouse insulin as a standard to estimate the plasma insulin levels. Plasma was analyzed for free fatty acids (FFA), triglycerides (TG), lactate and alanine transaminase (ALT) levels (Novartis Toxicology-Pathology Laboratory, E. Hanover, N.J.). Statistically significant differences ($p<0.05$) between study and control groups were determined using the Student's t-test and values were reported as mean ±SE.

Figure 6:
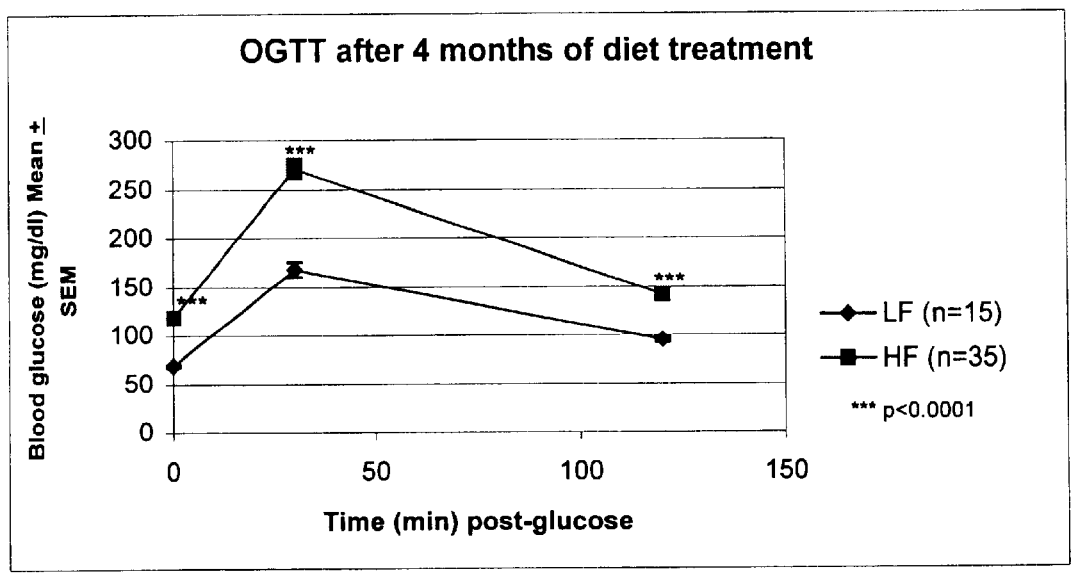
FIG. 6. C57 BU6J mice were maintained on a High-Fat (HF; 58% fat calories) or normal Low-Fat (LF; 10% fat calories) diet for at least four months to create a diabetic murine model. Mouse weights and levels of fasting blood glucose and insulin levels were determined. An oral glucose tolerance test (OGTT) was performed by administering a 1 g/kg glucose bolus via oral gavage (time 0) after collecting overnight fasting blood samples from the animals. Additional blood samples were collected at 30 and 120 minutes following glucose load. HF mice displayed an elevated fasting blood glucose level and showed an impaired glucose tolerance as compared to the age-matched LF control mice. Data are the means ±SE.

C57BU6J mice on a HF diet versus a low-fat diet (LF; 10.5% fat calories (lard), 73.1% carbodydrate, 16.5% protein calories) for 4 months were shown to have increased body weight (41.7±0.9 gm, n=35 vs. 27.5±0.3 gm, n=15). The HF mice developed mild diabetes as determined by elevated fasting blood glucose (157±4.3 vs. 98.9±6.9 mg/dl) and insulin (1826±214 vs. 725.9±149.2 pg/ml) levels and impaired glucose tolerance (FIG. 6). After 2 months on normal chow, the ob/ob mice became obese and developed mild diabetes. HF rats showed impaired glucose tolerance.

For post-mortem analysis, animals were weighed and sacrificed via $CO_2$ narcosis (or cervical dislocation) at 3–6 weeks following viral administration. Blood samples were removed via cardiac puncture and used for a complete blood analysis (Novartis Toxicology-Pharmacology, E. Hanover, N.J.). Whole livers were dissected free, weighed and liver sections were immediately frozen in either liquid nitrogen or dry ice for Oil red O staining or were fixed in formalin for hematoxylin & eosin (H & E) staining. The rest of the liver was snap frozen in liquid nitrogen and stored at −70° C. for later analyses (i.e. GK activity, glycogen, DNA, mRNA and protein). For GK activity assays, 200–300 mg of liver was added to 500 μl RIPA buffer (50 mM Tris-HCl, pH 7.5,150 mM NaCl, 2 mM EDTA, 1 mM EGTA, 0.1% Triton X-100, 10% glycerol) containing 10 μg/ml leupeptin, 10 μg/ml aprotinin, 25 μg/ml pefabloc and 1 mM PMSF. The tissue was homogenized (Kontes Duall tissue homogenizer) on ice for 30 sec and then sonicated on ice for 5 sec (twice). The sample was incubated for 10 min on ice and then centrifuged at 15,000× g at 4° C. for 5–10 min. The supernatant was removed and stored at −80° C. until use or diluted 1:10 in buffer (100 mM Tris-HCl, pH7.4, 100 mM KCl, 6 mM $MgCl_2$) and assayed for GK activity as described above.

Figure 10:
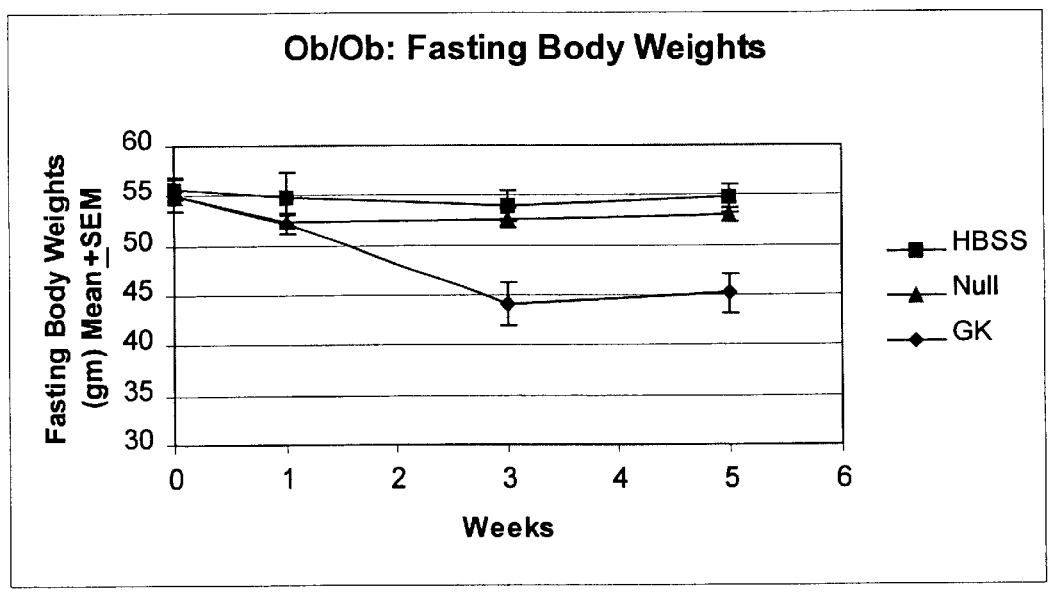
FIG. 10. Leptin deficient genetically obese ob/ob mice were treated with Av3hGK, Av3Null or HBSS. Their body weights were recorded before the treatment and 3 weeks following the vector treatment. Av3hGK treated mice showed a 20% reduction in their body weights ($p<0.001$; Students t-test).

Three weeks following administration of Av3hGK to HF mice there was a significant improvement in fasting blood glucose levels (95±4.8 mg/dl, $p<0.001$) when compared to Av3Null (135.4±5.9 mg/dl) and HBSS (134.2±8.0 mg/dl) treatments. Av3hGK treatment also reduced insulin levels (632±115 pg/ml, $p<0.01$) compared to control groups (Av3Null, 1083±291 pg/ml; HBSS, 1861±392 pg/ml) and improved glucose tolerance. Analyses of plasma lactate, FFA, TG, and ALT levels revealed no significant changes compared to control groups (FIG. 7). However, Av3hGK treatment lead to a sharp increase in liver weight (1.8 fold increase vs. HBSS at 3 weeks) and accumulation of fat in the liver (FIGS. 8 and 9). Two weeks following administration of Av3hGK to obese ob/ob mice, the animals displayed lowered blood glucose levels (HBSS: 181.8±10.7 mg/dl; Av3Null: 144.1±6.6 mg/dl; Av3hGK: 66.6±3.7 mg/dl), normalized glucose tolerance and lowered insulin levels (HBSS: 4900±1240 pg/ml; Av3Null: 2989±365 pg/mi; Av3hGK: 1113±228 pg/ml). Surprisingly, Av3hGK treatment resulted in a significant (>20%) reduction in body weight (before treatment: 55.1±1.6 gm; 3 weeks after treatment: 44.1±2.1 gm). These effects lasted for at least 5 weeks (FIG. 10). These results suggest that administration of GK should be beneficial for the treatment of obesity. However, as seen with HF mice, the liver weights of these mice were increased indicating that treatment with Av3hGK alone causes fat accumulation in the liver.

An OGTT performed at 2 weeks following viral administration to HF rats showed that Av3hGKRP treatment improved glucose tolerance as compared to HBSS and Av3Null (p<0.05) (FIG. 11). In addition, an improvement in fasting blood glucose levels was observed in HF C57BL/6J mice (8 months on diet) 3 weeks following administration of Av3hGKRP as compared to that seen with HBSS or Av3Null treatment (p<0.05) (FIG. 12). In contrast to findings with Av3hGK, treatment with Av3hGKRP did not result in an increase in liver weight or in the appearance of lipid vacuoles in the liver (FIGS. 8 and 9). The ability of Av3hGKRP to improve glucose tolerance was an unexpected finding, since GKRP is thought to function as an inhibitor of GK activity (Vandercammen and Van Schaftingen, Biochem. J. 294:551–556, 1993). Liver samples taken from either individual HF rats or groups of normal chow fed mice following 3 and 4 weeks of viral administration, respectively, showed that treatment with Av3hGKRP led to increased GK activity levels (assayed as described above) as compared to levels observed with HBSS or Av3Null (FIG. 13). These results suggest that overexpression of GKRP leads to stabilization of GK protein, thereby allowing more GK protein to be available following conditions of increased glucose (i.e. a meal). The lack of fat accumulation in livers of Av3hGKRP treated animals suggests that GKRP's ability to increase GK activity occurs in a physiologically regulated manner. Thus, adminstration of Av3hGKRP should lead to an improvement in glucose disposal following a meal but allow for normal glucose metabolism during fasting periods (low glucose), while avoiding the complications of hepatomegaly and lipid vacuole accumulation resulting from Av3hGK treatment. In addition, the ability of GKRP to increase GK activity suggests that administration of GKRP should be beneficial for the treatment of obesity.

Example 2

Lowering Fasting Blood Glucose Levels By Co-administration of GK and GKRP in Separate Vectors The effects of co-administration of GKRP and GK on lowering fasting blood glucose levels and improving glucose tolerance were tested in male C57B/6, mice, maintained on a high-fat diet for at least 4 months or on a normal chow diet, and in high-fat fed Sprague-Dawley rats (see example 1 for animal handling and diet compositions).

Recombinant adenoviruses Av3hGK and Av3hGKRP, encoding the full-length cDNAs for human liver GK and human GKRP, respectively, and Av3Null (lacks a transgene) were generated and amplified exactly as described in example 1.

To determine the most effective ratio of Av3hGK to Av3hGKRP to use for in vivo studies preliminary in vitro experiments were carried out. Primary rat hepatocytes were infected with a total of 200 particles/cell (see Example 1) of Av3hGK and Av3hGKRP in the following ratios: 1:10; 1:5; 1:3; 1:2; 1:1; 2:1; 3:1; 5:1; and 10:1, with 200 particles/cell of Av3Null or left untreated. GK enzymatic activity was determined from cell lysates two days following infection (see example 1), and the vector ratio producing the highest in vitro GK activity was used for subsequent in vivo experiments.

Five groups of mice (n=5–15/group) were administered the adenoviral vectors via tail vein injection (see example 1) at a total dose of $1.2 \times 10^{11}$ particles/animal (in a final volume of 250–500 µl of sterile HBSS). Each group was treated with either: (1) Av3hGKRP mixed with Av3Null ($6 \times 10^{10}$ particles/each); (2) Av3hGK mixed with Av3Null ($6 \times 10^{10}$ particles/each); (3) Av3hGKRP mixed with Av3hGK ($6 \times 10^{10}$ particles/each); (4) Av3Null ($1.2 \times 10^{11}$ particles); or (5) HBSS. The dose of each vector administered was based on an optimal ratio of 1:1 for Av3hGK to Av3hGKRP. Normal chow fed mice were administered the same combinations of vector (ratio of 1:1) but at a total dose of $0.6 \times 10^{11}$ particles/animal. OGTTs were performed at 1 week before or at 1, 2 and 3 weeks following viral administration. Body weights of overnight fasted mice were recorded and blood (50 µl) was collected via tail nick bleeds or from retro-oribital sinus in heparin fluoride and lithium coated tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were administered the same combinations of adenoviral vectors (ratio of 1:1) as mice, except at a total dose of $1.2 \times 10^{12}$ particles/animal in a final volume of 750 µl sterile HBSS. OGTTs were performed at 1, 2, and 3 weeks following viral administration. Body weights of overnight fasted rats were recorded and 500 µl of blood was collected (via jugular catheter) in EDTA/aprotinin tubes. A glucose bolus (1g/kg body weight) was then administered by an oral gavage (at time 0 min). Blood (500 µl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

Mice and rats were sacrificed and a complete post-mortem analysis was performed at 4 weeks following vector administration as described in example 1. The beneficial effects of co-administration of Av3hGK and Av3hGKRP were compared to treatment with Av3hGK or Av3h GKRP alone. Administration of Av3hGKRP was shown to lower fasting blood glucose levels and/or improve glucose tolerance and lead to an increase in GK activity in diabetic mice (HF fed) and in high-fat fed rats (see example 1). The beneficial effects occurred without resulting in an increase in liver weight or in fat accumulation in the livers of Av3hGKRP treated animals, as compared to treatment with Av3hGK alone (FIGS. 8 and 9). It is expected that administration of GKRP with GK will provide a means of controlling the increased GK activity in a physiologically relevant manner, i.e. improve glucose disposal following a meal, but allow for normal glucose metabolism during fasting periods (inhibit GK activity under conditions of low glucose). Since Av3hGKRP treatment results in an increase in GK activity itself (i.e. possible by stabilizing GK protein), for co-administration, lower doses of Av3hGK would therefore be required for improving fasting blood glucose levels thereby further minimizing adverse effects on the liver (i.e. hepatomegaly and fat accumulation). It is thus expected that the effective total mixed viral dose will be less (and thus less potential toxicity) than with either virus alone. Av3hGK treatment was shown to reduce body weight in obese ob/ob mice, but lead to an increase in liver weight (see example 1). Therefore, it is expected that administration of GKRP with GK should also be beneficial for the treatment of obesity.

Example 3

Lowering Fasting Blood Glucose Levels By Co-administration of GK and GKRP in a Single Vector The effects of co-administration of GKRP and GK on lowering fasting blood glucose levels and improving glucose tolerance were tested in male C57B/6 mice, maintained on a high-fat diet for at least 4 months or on a normal chow diet, and in high-fat fed Sprague-Dawley rats (see example 1 for animal handling and diet compositions).

Figure 14:
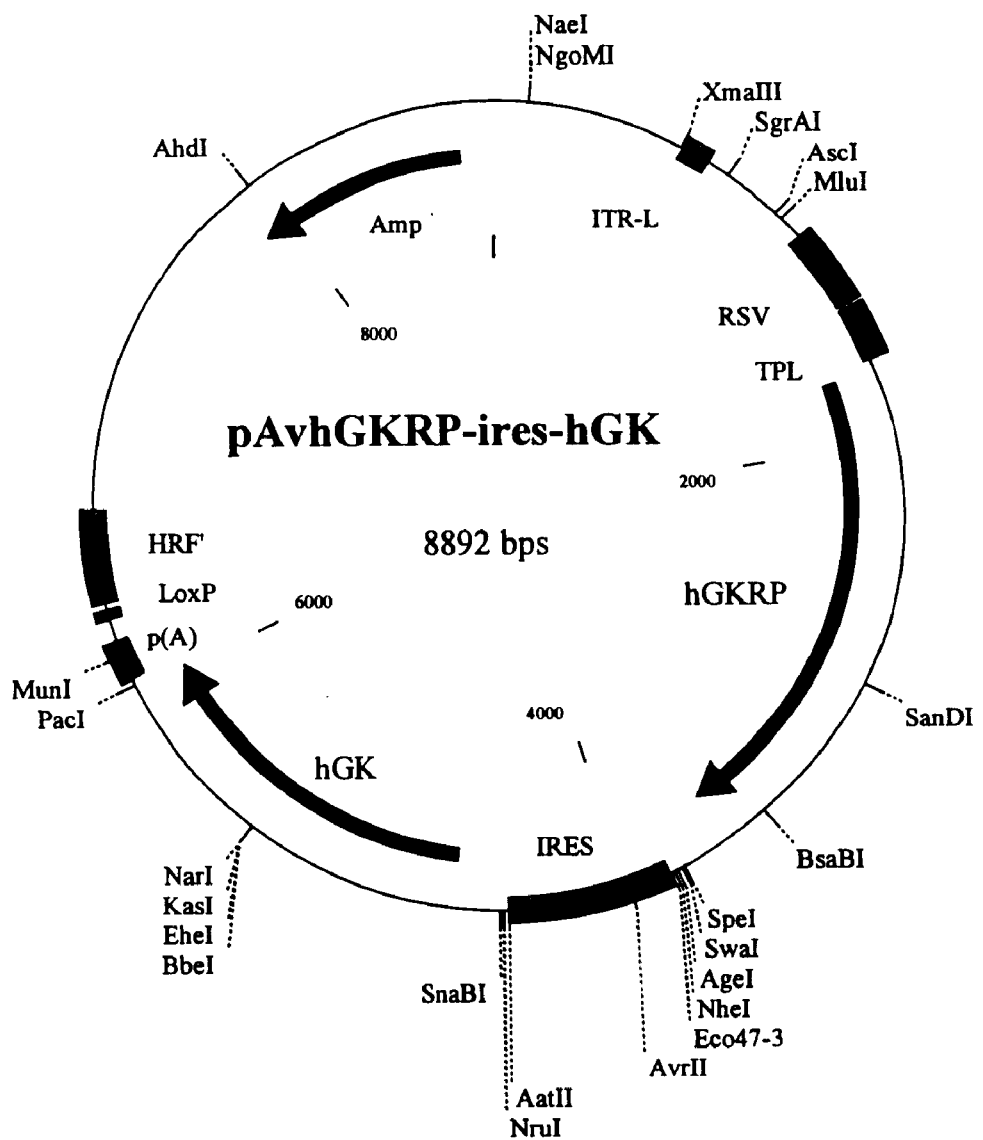
FIG. 14. Schematic diagram of the adenovirus shuttle plasmid, pAvhGKRP-ires-hGK, used in construction of the Av3hGKRP-ires-hGK (FIG. 3) adenoviral vector.
Figure 15:
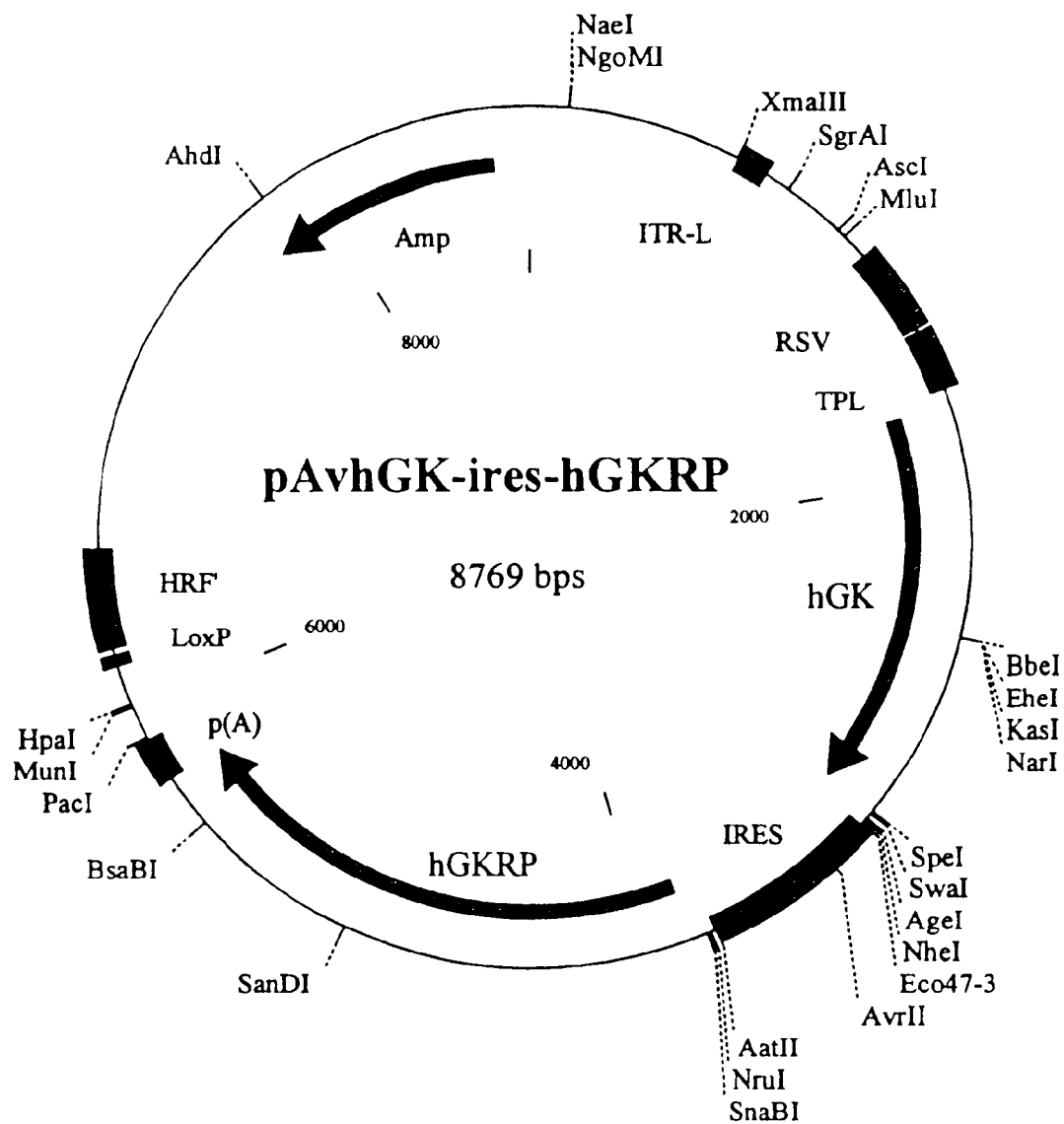
FIG. 15. Schematic diagram of the adenovirus shuttle plasmid, pAvhGK-ires-hGKRP, used in construction of the Av3hGK-ires-hGKRP (FIG. 3) adenoviral vector.

The plasmid pAViresMCS, obtained from R. Mowa (Novartis Pharmaceuticals, Basel, CH), was generated by inserting a PCR fragment containing the internal ribosomal entry site (IRES) from pIRES2 (Invitrogen, Carlsbad, Calif.) into pBSitrIoxnMCS (an adenoviral shuttle plasmid containing a lox site essentially identical to pAvS6alx described in example 1). A 2 kb BamHI fragment containing the full-length cDNA encoding human GKRP was excised from pAvhGKRPIx (see example 1) and ligated to pAViresMCS digested with BamHI to generate pAvS6alx-hGKRP-ires. A 1.4 kb fragment containing the full-length CDNA encoding human liver GK was excised from pGEX4T-1-hGK (see example 1) with EcoRI-SalI, klenow-filled, and ligated into the EcoRV site of pAvS6alx-hGKRP-ires to create pAvhGKRP-ires-hGK (FIG. 14). To generate pAvS6alx-hGK-ires, the 1.4 kb EcoRI-SalI fragment encoding hGK, excised from pGEX4T-1-hGK, was klenow-filled and ligated to pAViresMCS which was digested with SpeI and klenow-filled. The 2 kb BamHl fragment containing hGKRP (as above) was klenow-filled and ligated to EcoRV digested pAvS6alx-hGK-ires to generate pAvhGK-ires-hGKRP (FIG. 15). The orientation of the inserts was confirmed by restriction analysis and DNA sequencing. Generation and amplification of the recombinant adenoviruses Av3hGKRP-ires-hGK, Av3hGK-ires-hGKRP, and Av3Null (lacks a transgene) was performed exactly as described in example 1.

Six groups of HF mice (n=5–15/group) were administered the adenoviral vectors via tail vein injection (see example 1) at a dose of $1.2 \times 10^{11}$ particles/animal (in a final volume of 100 µl sterile HBSS). Each group was treated with either: (1) Av3hGK; (2) Av3hGKRP; (3) Av3hGKRP-ires-hGK; (4) Av3hGK-ires-hGKRP; (5) Av3Null ($1.2 \times 10^{11}$ particles); or (6) HBSS. Normal chow fed mice were administered the same vectors but at a total dose of $0.6 \times 10^{11}$ particles/animal. OGTTs were performed at 1 week before or at 1, 2 and 3 weeks following viral administration. Body weights of overnight fasted mice were recorded and blood (50 µl) was collected via tail nick bleeds or from retro-oribital sinus in heparin fluoride and lithium coated tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were each administered the same adenoviral vectors as mice, except at a dose of $1.2 \times 10^{12}$ particles/animal in a final volume of 750 µl sterile HBSS. OGTTs were performed at 1, 2, and 3 weeks following viral administration. Body weights of overnight fasted rats were recorded and 500 µl of blood was collected (via jugular catheter) in EDTA/aprotinin tubes. A glucose bolus (1 g/kg body weight) was then administered by an oral gavage (at time 0 min). Blood (500 µl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

Mice and rats were sacrificed and a complete post-mortem analysis was performed at 4 weeks following vector administration as described in example 1. The effects of co-administration of GK and GKRP from a single vector (bicistronic), Av3hGK-ires-hGKRP or Av3hGKRP-ires-hGK, were compared to treatment with Av3hGK or Av3hGKRP alone. As indicated in example 2, it is expected that administration of GKRP with GK would have the beneficial effect of controlling the increased GK activity in a physiologically relevant manner (as well as reducing fat accumulation in the liver observed with Av3hGK treatment alone).

Example 4

Reduction of Hepatic Triglyceride Accumulation by Co-administration of GK and UCP3 in Separate Vectors The effects of co-administration of GK and UCP3 on reducing triglyceride accumulation in liver resulting from treatment with GK alone were tested in male C57BL/6 mice, maintained on a high-fat diet for at least 4 months or on a normal chow diet, and in high-fat fed Sprague-Dawley rats (see example 1 for animal handling and diet compositions).

Figure 16:
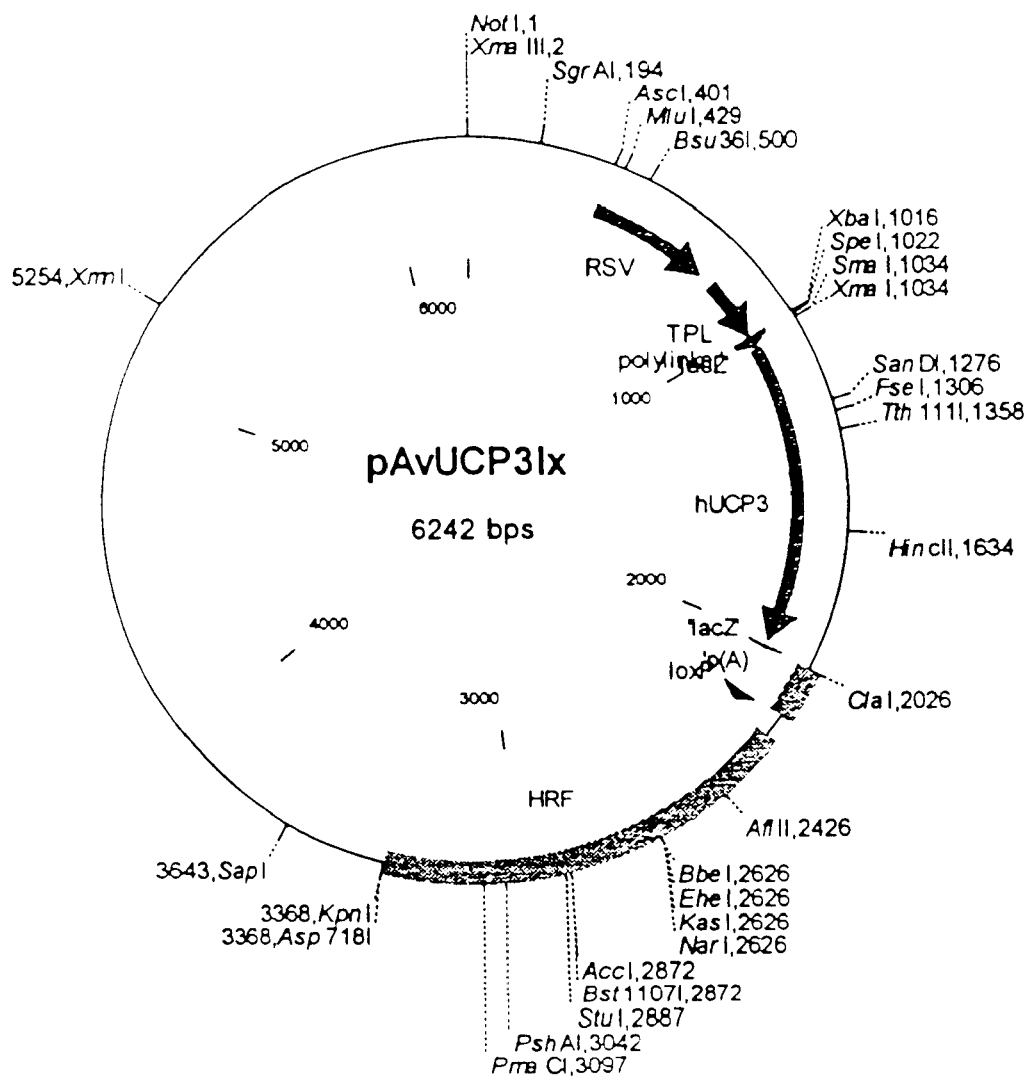
FIG. 16. Schematic diagram of the adenovirus shuttle plasmid, pAvUCP3ix, used in construction of the Av3hUCP3 (FIG. 3) adenoviral vector.

The plasmid pBSIISKUCP3 was obtained from Drs. Giacobino and Muzzin (Univ. of Geneva, CH). The SpeI-ClaI fragment, containing the full-length cDNA encoding human UCP3 (Boss et al., FEBS Lett. 408:3942, 1997) was excised from this plasmid, gel purified and ligated to the adenoviral shuttle vector containing a lox site, pAvS6alx (see example 1), digested with SpeI-ClaI to form pAvhUCP3ix (FIG. 16). Generation and amplification of recombinant adenoviruses encoding UCP3 (Av3hUCP3) and human liver GK (Av3hGK) and Av3Null (lacks a transgene) was performed exactly as described in example 1.

Five groups of HF mice (n=5–15/group) were administered the adenoviral vectors via tail vein injection (see example 1) at a total dose of $1.2 \times 10^{11}$ particles/animal (in a final volume of 250–500 µl of sterile HBSS). Each group was treated with either: (1) Av3hGK mixed with Av3Null ($6 \times 10^{10}$ particles/each); (2) Av3hUCP3 mixed with Av3Null ($6 \times 10^{10}$ particles/each); (3) Av3hGK mixed with Av3hUCP3 ($6 \times 10^{10}$ particles/each); (4) Av3Null ($1.2 \times 10^{11}$ particles); or (5) HBSS. The dose of each vector administered was based on an optimal ratio of 1:1 for Av3hGK to Av3hUCP3. Normal chow fed mice were administered the same combinations of vector (ratio of 1:1) but at a total dose of $0.6 \times 10^{11}$ particles/animal. OGTTs were performed at 1 week before or at 1, 2 and 3 weeks following viral administration. Body weights of overnight fasted mice were recorded and blood (50 µl) was collected via tail nick bleeds or from retro-oribital sinus in heparin fluoride and lithium coated tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were administered the same combinations of adenoviral vectors (ratio of 1:1) as mice, except at a total dose of $1.2 \times 10^{12}$ particles/animal in a final volume of 750 µl sterile HBSS. OGTTs were performed at 1, 2, and 3 weeks following viral administration. Body weights of overnight fasted rats were recorded and 500 µl of blood was collected (via jugular catheter) in EDTA/aprotinin tubes. A glucose bolus (1 g/kg body weight) was then administered by an oral gavage (at time 0 min). Blood (500 µl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

Mice and rats were sacrificed and a complete post-mortem analysis was performed at 4 weeks following vector administration as described in example 1. The effects of co-administration of Av3hGK and Av3hUCP3 were compared to treatment with Av3hGK alone. As described in example 1, administration of Av3hGK improves glucose tolerance in diabetic mice and in glucose impaired rats, but leads to fat accumulation in the liver and hepatomegaly. Since UCP proteins function to regulate lipid metabolism and are mediators of thermogenesis (Samec et al., FASEB J. 12, 715–724, 1998), it is expected that administration of UCP3 with GK would have the beneficial effect of reducing the fat accumulation in the liver by converting the excess energy to heat. Therefore, co-administration of GK and UCP3 should lead to improved glucose tolerance and be beneficial for the treatment of obesity.

Example 5

Reduction of Hepatic Triglyceride Accumulation by Co-administration of GK and UCP3 in a Single Vector The effects of co-administration of GK and UCP3 on reducing triglyceride accumulation in liver resulting from treatment with GK alone were tested in male C57BL/6 mice, maintained on a high-fat diet for at least 4 months or on a normal chow diet, and in high-fat fed Sprague-Dawley rats (see example 1 for animal handling and diet compositions).

Figure 17:
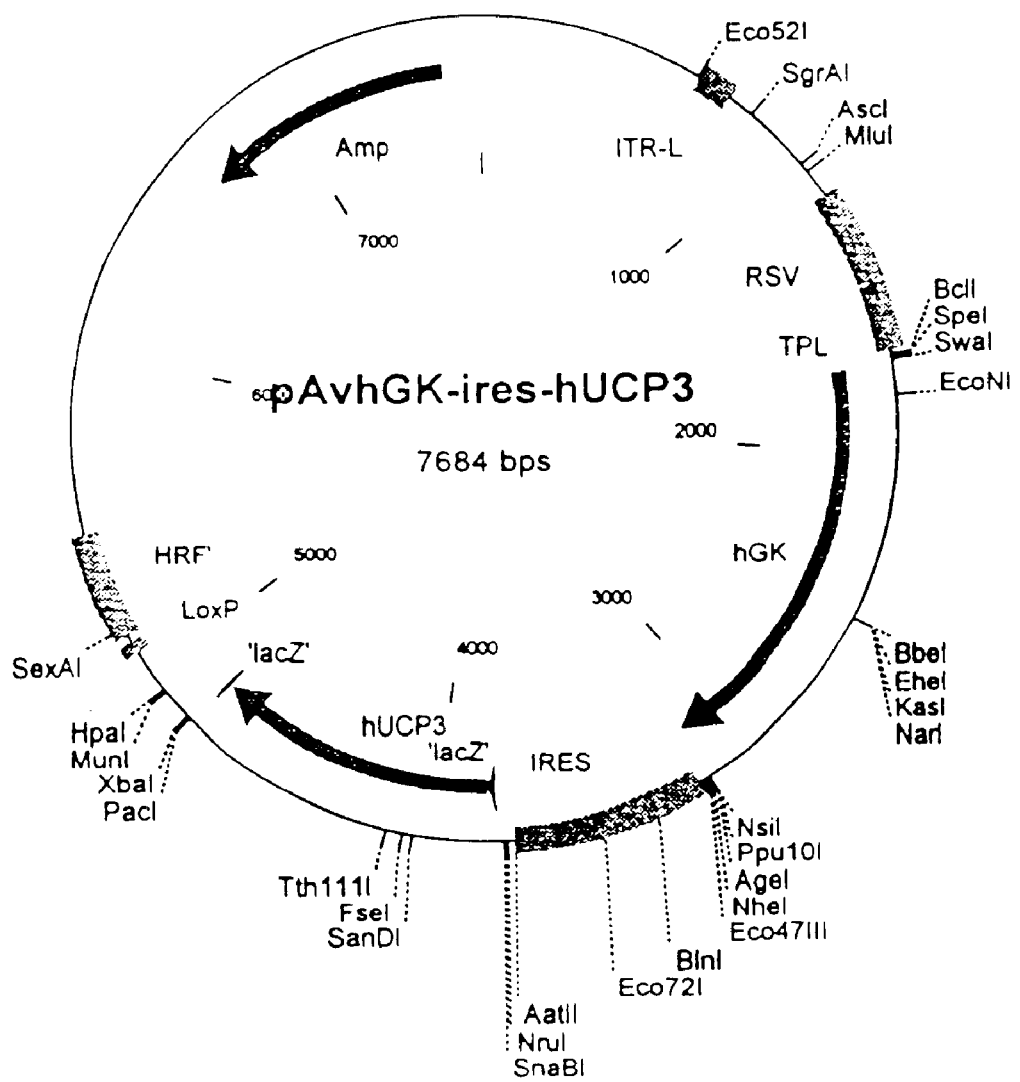
FIG. 17. Schematic diagram of the adenovirus shuttle plasmid, pAvhGK-ires-hUCP3, used in construction of the Av3hGK-ires-hUCP3 (FIG. 3) adenoviral vector.
Figure 18:
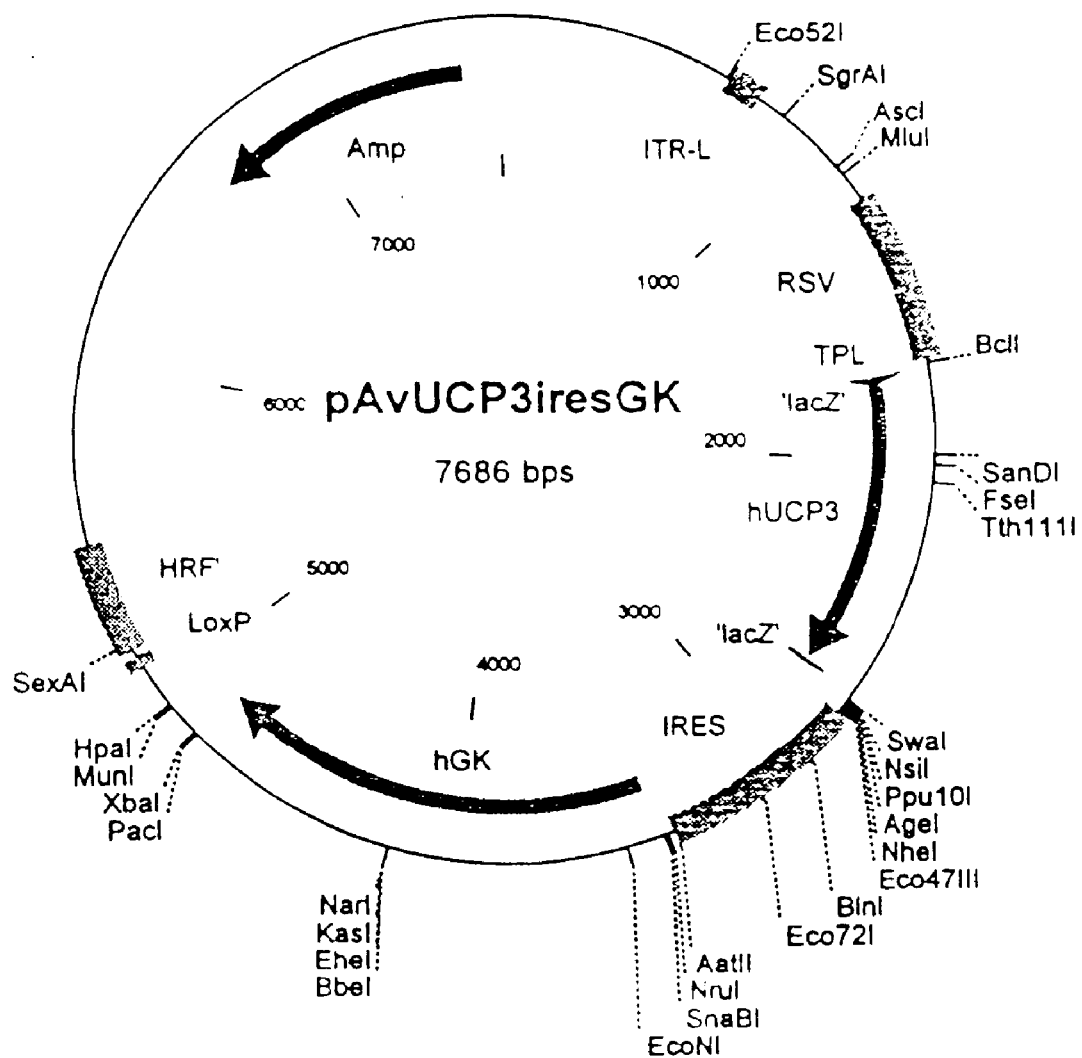
FIG. 18. Schematic diagram of the adenovirus shuttle plasmid, pAvhUCP3-ires-hGK, used in construction of the Av3hUCP3-ires-hGK (FIG. 3) adenoviral vector.

The plasmid pAViresMCS was generated as described in example 3. The adenoviral shuttle vector, pAvs6alx-hGK-ires, containing the full-length cDNA (1.4 kb) encoding human liver GK was constructed as described in example 3. A 1 kb fragment containing the full-length cDNA encoding human UCP3 was excised from pAvUCP31x (see example 4) with SpeI and ClaI, klenow-filled, and ligated into the EcoRV site of pAvS6alx-hGK-ires to create the adenoviral shuttle vector pAvhGK-ires-hUCP3 (FIG. 17). To generate pAvS6alx-hUCP3-ires, the 1 kb SpeI-ClaI, klenow-filled UCP3 fragment ligated pAViresMCS which was digested with SpeI and klenow-filled. The 1.4 kb EcoRI-SalI fragment containing the full-length cDNA encoding human GK was excised from pGEX4T-1-hGK (see example 1) and ligated to EcoRV digested pAvS6alx-hUCP2-ires to generate the adenoviral shuttle vector pAvhUCP3-ires-hGK (FIG. 18). The orientation of the inserts was confirmed by restriction analysis and DNA sequencing. Generation and amplification of the recombinant adenoviruses Av3hGKireshUCP3, Av3hUCP3ireshGK, Av3hGK, Av3hUCP3 (see example 4) and Av3Null (lacks a transgene) were performed exactly as described in example 1.

Six groups of HF mice (n=5–15/group) were administered the adenoviral vectors via tail vein injection (see example 1) at a dose of $1.2 \times 10^{11}$ particles/animal (in a final volume of 100 µl sterile HBSS). Each group was treated with either: (1) Av3hGK; (2) Av3hUCP3; (3) Av3hGK-ires-hUCP3; (4) Av3hUCP3-ires-hGK; (5) Av3Null ($1.2 \times 10^{11}$ particles); or (6) HBSS. Normal chow fed mice were administered the same vectors but at a total dose of $0.6 \times 10^{11}$ particles/animal. OGTTs were performed at 1 week before or at 1, 2 and 3 weeks following vector administration. Body weights of overnight fasted mice were recorded and blood (50 µl) was collected via tail nick bleeds or from retro-oribital sinus in FI/EDTA tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were each administered the adenoviral vectors as mice, except at a dose of $1.2 \times 10^{12}$ particles/animal in a final volume of 750 µl sterile HBSS. OGTTs were performed at 1, 2, and 3 weeks following vector administration. Body weights of overnight fasted rats were recorded and 500 µl of blood was collected (via jugular catheter) in EDTA/aprotinin tubes. A glucose bolus (1 g/kg body weight) was then administered by an oral gavage (at time 0 min). Blood (500 µl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

Mice and rats were sacrificed and a complete post-mortem analysis was performed at 4 weeks following vector administration as described in example 1. The effects of co-administration of GK and UCP3 from a single vector (bicistronic), Av3hGK-ires-hUCP3 or Av3hUCP3-ires-hGK, were compared to treatment with Av3hGK or Av3hUCP3 alone. As described in example 4, it is expected administration of Av3hUCP3 with Av3hGK would have the beneficial effect of reducing the fat accumulation in the liver resulting from Av3hGK treatment alone. Co-administration of GK and UCP3 should lead to improved glucose tolerance and be beneficial for the treatment of obesity.

Example 6

Reduction of Hepatic Triglyceride Accumulation by Co-administration of GK and UCP2 in Separate Vectors The effects of co-administration of GK and UCP2 on reducing triglyceride accumulation in liver resulting from treatment with GK alone were tested in male C57BL/6 mice, maintained on a high-fat diet for at least 4 months or on a normal chow diet, and in high-fat fed Sprague-Dawley rats (see example 1 for animal handling and diet compositions).

Figure 19:
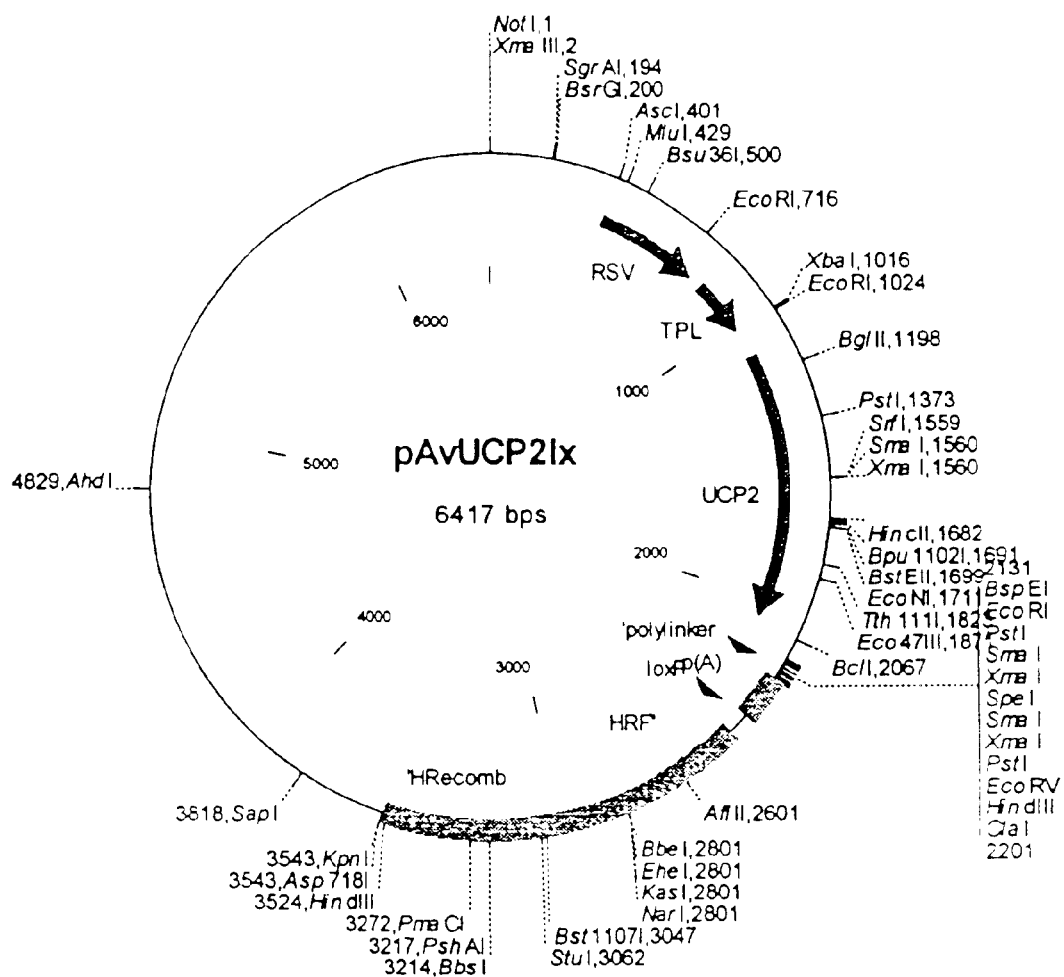
FIG. 19. Schematic diagram of the adenovirus shuttle plasmid, pAvhUCP2ix, used in construction of the Av3hUCP2 (FIG. 3) adenoviral vector.

The plasmid pBSIIKSUCP2 containing the full-length cDNA encoding human UCP2 (1.1 kb, Fleury et al., Nat. Genet. 15:269–272, 1997) was obtained from Drs. Giacobino and Muzzin (Univ. of Geneva, CH). This plasmid was digested with XbaI, klenow-filled and the digested with SpeI. The resulting 1.1 kb fragment was purified from an agarose gel and ligated to the adenoviral shuttle vector containing a lox site, pAvS6alx (see example 1), digested with EcoRV and SpeI to form pAvhUCP2lx (FIG. 19). Generation and amplification of recombinant adenoviruses encoding UCP2 (Av3hUCP2), human liver GK (Av3hGK) and Av3Null (lacks a transgene) and were performed exactly as described in example 1.

Five groups of HF mice (n=5–15/group) were administered the adenoviral vectors via tail vein injection (see example 1) at a total dose of $1.2 \times 10^{11}$ particles/animal (in a final volume of 250–500 µl of sterile HBSS). Each group was treated with either: (1) Av3hGK mixed with Av3Null ($6 \times 10^{10}$ particles/each); (2) Av3hUCP2 mixed with Av3Null ($6 \times 10^{10}$ particles/each); (3) Av3hGK mixed with Av3hUCP2 ($6 \times 10^{10}$ particles/each); (4) Av3Null ($1.2 \times 10^{11}$ particles); or (5) HBSS. The dose of each vector administered was based on an optimal ratio of 1:1 for Av3hGK to Av3hUCP2. Normal chow fed mice were administered the same combinations of vector (ratio of 1:1) but at a total dose of $0.6 \times 10^{11}$ particles/animal. OGTTs were performed at 1 week before or at 1, 2 and 3 weeks following vector administration. Body weights of overnight fasted mice were recorded and blood (50 µl) was collected via tail nick bleeds or from retro-oribital sinus in heparin fluoride and lithium coated tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were administered the same combinations of vectors (ratio of 1:1) as mice, except at a total dose of $1.2 \times 10^{12}$ particles/animal in a final volume of 750 µl sterile HBSS. OGTTs were performed at 1, 2, and 3 weeks following viral administration. Body weights of overnight fasted rats were recorded and 500 µl of blood was collected (via jugular catheter) in EDTA/aprotinin tubes. A glucose bolus (1 g/kg body weight) was then administered by an oral gavage (at time 0 min). Blood (500 µl) was collected exactly at times 0, 1, 3, 5, 10, 15, 20 30, 45, 60, 75 and 90 min. After each blood sample was taken, an equal volume of blood from a donor rat was injected into the rat to maintain normal blood pressure.

Mice were sacrificed and a complete post-mortem analysis was performed at 4 weeks following vector administration as described in example 1. The effects of co-administration of Av3hGK and Av3hUCP2 were compared to treatment with Av3hGK alone. As described in example 1, administration of Av3hGK improves glucose tolerance in diabetic mice and in glucose impaired rats, but leads to fat accumulation in the liver and hepatomegaly. Since UCP proteins function to regulate lipid metabolism and is a mediator of thermogenesis (Samec, S. et al., FASEB J. 12, 715–724, 1998), it is expected administration of Av3hUCP2 with Av3hGK would have the beneficial effect of reducing the fat accumulation in the liver resulting from Av3hGK treatment alone. Co-administration of GK and UCP2 should lead to improved glucose tolerance and be beneficial for the treatment of obesity.

Example 7

Reduction of Hepatic Triglyceride Accumulation by Co-administration of GK and UCP2 in a Single Vector The effects of co-administration of GK and UCP2 on reducing triglyceride accumulation in liver resulting from treatment with GK alone were tested in male C57BL/6 mice, maintained on a high-fat diet for at least 4 months or on a normal chow diet, and in high-fat fed Sprague-Dawley rats (see example 1 for animal handling and diet compositions).

Figure 20:
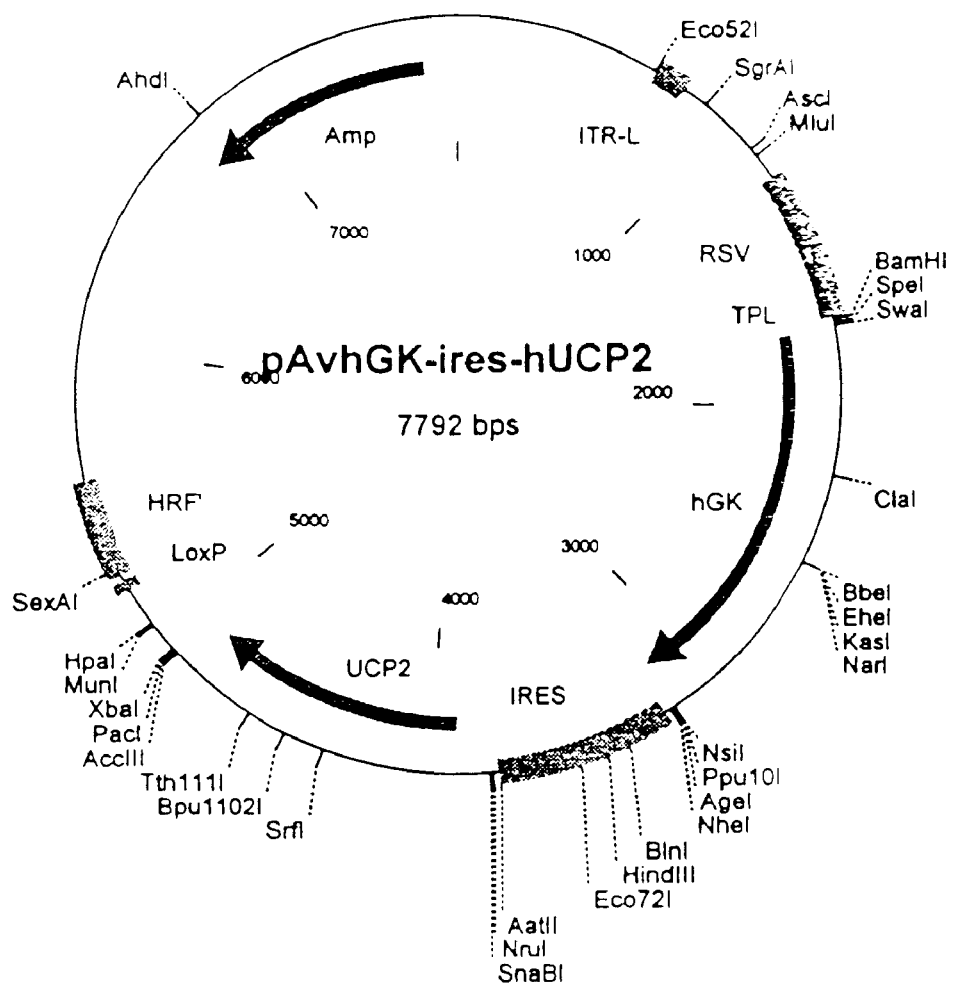
FIG. 20. Schematic diagram of the adenovirus shuttle plasmid, pAvhGK-ires-hUCP2, used in construction of the Av3hGK-ires-hUCP2 (FIG. 3) adenoviral vector.
Figure 21:
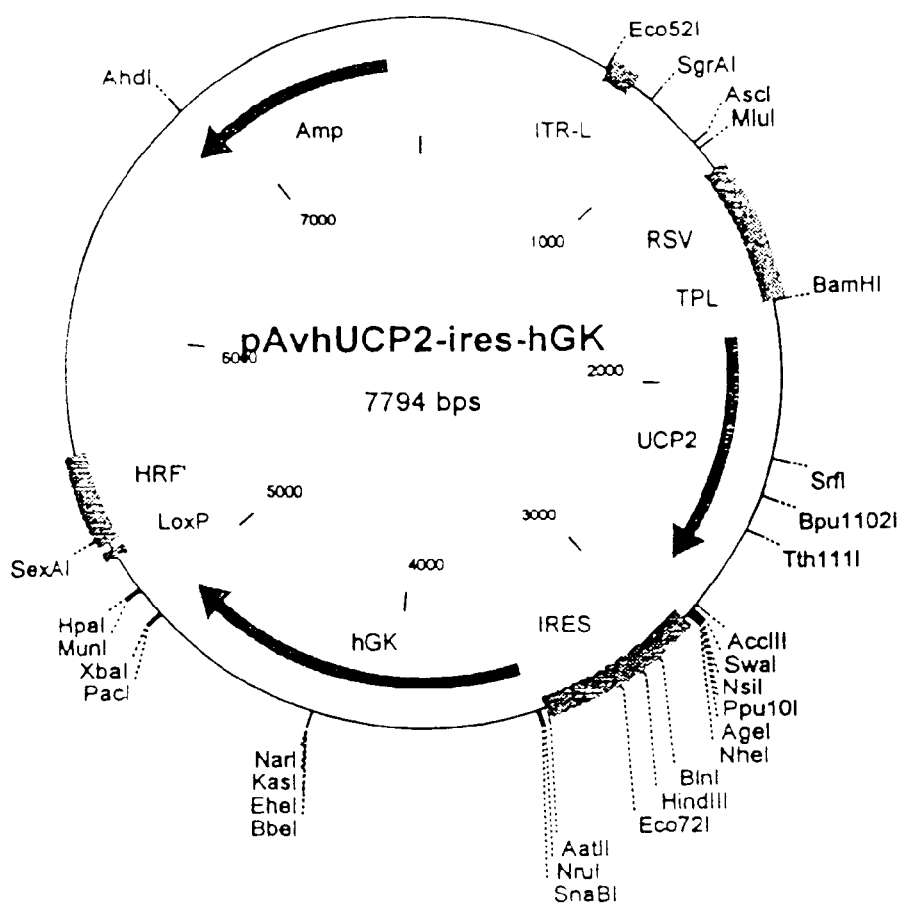
FIG. 21. Schematic diagram of the adenovirus shuttle plasmid, pAvhUCP2-ires-hGK, used in construction of the Av3hUCP2-ires-hGK (FIG. 3) adenoviral vector.

The plasmid pAViresMCS was generated as described in example 3. A 1.4 kb EcoRI-SalI fragment containing the full-length cDNA encoding human liver GK was excised from pGEX-4T-1-hGK (see example 1), klenow-filled and ligated to pAViresMCS which was digested with ClaI and klenow-filled to generate pAvS6alx-hGK-ires. A 1.1 kb fragment containing the full-length cDNA encoding human UCP2 was excised from pBSIIKSUCP2 (see example 6) with EcoRI, klenow-filled, and ligated into the EcoRV site of pAvS6alx-hGK-ires to create pAvS6alx-hGK-ires-hUCP2 (FIG. 20). To generate pAvS6alx-hUCP2-ires, the 1.1 kb EcoRI, klenow-filled UCP2 fragment was ligated to pAViresMCS which was digested with SpeI and klenow-filled. The 1.4 kb EcoRI-SalI, klenow-filled hGK fragment was was then ligated to EcoRV digested pAvS6alx-hUCP2-ires to generate pAvS6alx-hUCP2-ires-hGK (FIG. 21). The orientation of the inserts was confirmed by restriction analysis and DNA sequencing. Generation and amplification of the recombinant adenoviruses Av3hGK-ires-hUCP2, Av3hUCP2-ires-hGK, Av3hGK, Av3UPC2 (see example 6) and Av3Null (lacks a transgene) was performed exactly as described in example 1.

Six groups of mice (n=5–15/group) were administered the adenoviral vectors via tail vein injection (see example 1) at a dose of $1.2 \times 10^{11}$ particles/animal (in a final volume of 100 µl sterile HBSS). Each group was treated with either: (1) Av3hGK; (2) Av3hUCP2; (3) Av3hGK-ires-hUCP2; (4) Av3hUCP2-ires-hGK; (5) Av3Null ($1.2 \times 10^{11}$ particles); or (6) HBSS. Normal chow fed mice were administered the same vectors but at a total dose of $0.6 \times 10^{11}$ particles/animal. OGTTs were performed at 1 week before or at 1, 2 and 3 weeks following vector administration. Body weights of overnight fasted mice were recorded and blood (50 µl) was collected via tail nick bleeds or from retro-oribital sinus in heparin fluoride and lithium tubes. A glucose bolus (1 g/kg body weight) was then administered by oral gavage (at time 0 min). Blood (50 µl) was collected exactly at time 30 and 120 min.

Viral dosing of rats was performed via jugular venous catheters as described in example 1. Five groups of rats (n=5–15) were each administered the adenoviral vectors as mice, except at a dose of $1.2 \times 10^{12}$ particles/animal in a final volume of 750 µl sterile HBSS. OGTTs were performed at 1, 2, and 3 weeks following vector administration. Body weights of overnight fasted rats were recorded and 500 µl of blood was collected (via jugular catheter) in EDTA/aprotinin tubes. A glucose bolus (1 g/kg body weight) was then administered by an oral gavage (at time 0 min). Blood (500 µl) was collected exactly at times 0,1, 3, 5, 10, 15, 20 30, 45, 60, 75 and 90 min. After each blood sample was taken, an equal volume of blood from a donor rat was injected into the rat to maintain normal blood pressure.

Mice were sacrificed and a complete post-mortem analysis was performed at 4 weeks following vector administration as described in example 1. The effects of co-administration of GK and UCP2 from a single vector (bicistronic), Av3hGK-ires-hUCP2 or Av3hUCP2-ires-hGK, were compared to treatment with Av3hGK or Av3hUCP2 alone. As described in example 6, it is expected administration of Av3hUCP2 with Av3hGK would have the beneficial effect of reducing the fat accumulation in the liver resulting from Av3hGK treatment alone. Co-administration of GK and UCP2 should lead to improved glucose tolerance and be beneficial for the treatment of obesity.

Although the present invention has been described in considerable detail with reference to certain preferred versions thereof, other versions are possible without departing from the spirit and scope of the preferred versions contained herein. All references and Patents (U.S. and others) referred to herein are hereby incorporated by reference in their entirety as if set forth in full herein.

What is claimed is:

1. A method of treating diabetes comprising intravenously administering to a pateint in need thereof a therapeutically effective amount of an adenoviral vector comprising a polynucleotide sequence encoding glucokinase regulatory protein (GKRP) such that the adenoviral vector transduces hepatocytes of the patient to express GKRP, whereby at least one symptom of diabetes is alleviated.

2. The method of claim 1 wherein the adenoviral vector also encodes a polynucleotide sequence encoding glucokinase (GK).

3. The method of claim 1 wherein diabetes includes type 1 and type 2 diabetes.

4. A method of reducing elevated blood glucose levels in a patient comprising intravenously administering an adenoviral vector comprising a polynucleotide sequence encoding GKRP such that the adenoviral vector transduces hepatic cells in vivo and the cells are modified to produce GKRP, whereby the elevated blood glucose levels are reduced.

5. A method of reducing elevated blood glucose levels in a patient comprising intravenously administering an adenoviral vector comprising a polynucleotide sequence encoding GKRP and GK such that the adenoviral vector transduces hepatic cells in vivo and the cells are modified to produce GKRP and GK, whereby the elevated blood glucose levels are reduced.

6. A method of treating diabetes comprisng intravenously administering to a patient in need thereof a therapeutically effective amount of a first adenoviral vector comprising a polynucleotide sequence encoding glucokinase regulatory protein (GKRP) and a second adenoviral vector comprising a polynucleotide sequence encoding glucokinase (GK) such that the adenoviral vectors transduce hepatocytes of the patient to express GKRP and GK, whereby at least one symptom of diabetes is alleviated.

7. The method of claim 6 wherein the diabetes is type 1 or type 2 diabetes.

8. The method of claim 4 further comprising an additional adenoviral vector comprising a polynucleotide sequence encoding GK such that the hepatic cells of the patient produce GKRP and GK.

* * * * *

SEQUENCE LISTING

```
<160> NUMBER OF SEQ ID NOS: 10

<210> SEQ ID NO 1
<211> LENGTH: 1231
<212> TYPE: DNA
<213> ORGANISM: Unknown
<220> FEATURE:
<223> OTHER INFORMATION: cDNA from clone UCP3L
```

-continued

```
<400> SEQUENCE: 1
tcctgggatg gagccctagg gagcccctgt gctgcccctg ccgtggcagg actcacagcc      60
ccaccgctgc actgaagccc aggctgtgg agcagcctct ctccttggac ctcctctcgg      120
ccctaaaggg actgggcaga gccttccagg actatggttg gactgaagcc ttcagacgtg      180
cctcccacca tggctgtgaa gttcctgggg gcaggcacag cagcctgttt tgctgacctc      240
gttacctttc cactggacac agccaaggtc cgcctgcaga tccagggga gaaccaggcg      300
gtccagacgg cccggctcgt gcagtaccgt ggcgtgctgg gcaccatcct gaccatggtg      360
cggactgagg gtccctgcag ccctacaat gggctggtgg ccggcctgca gcgccagatg      420
agcttcgcct ccatccgcat cggcctctat gactccgtca gcaggtgta caccccaaa      480
ggcgcggaca actccagcct cactacccgg attttggccg gctgcaccac aggagccatg      540
gcggtgacct gtgcccagcc cacagatgtg gtgaaggtcc gatttcaggc cagcatacac      600
ctcgggccat ccaggagcga cagaaaatac agcgggacta tggacgccta cagaaccatc      660
gccaggagg aaggagtcag gggcctgtgg aaaggaactt tgcccaacat catgaggaat      720
gctatcgtca actgtgctga ggtggtgacc tacgacatcc tcaaggagaa gctgctggac      780
taccacctgc tcactgacaa cttcccctgc cactttgtct ctgcctttgg agccggcttc      840
tgtgccacag tggtggcctc cccggtggac gtggtgaaga cccggtatat gaactcacct      900
ccaggccagt acttcagccc cctcgactgt atgataaaga tggtggccca ggagggcccc      960
acagccttct acaagggatt tacaccctcc tttttgcgtt tgggatcctg gaacgtggtg      1020
atgttcgtaa cctatgagca gctgaaacgg gccctgatga agtccagat gttacgggaa      1080
tcaccgtttt gaacaagaca agaaggccac tggtagctaa cgtgtccgaa accagttaag      1140
aatggaagaa acggtgcat ccacgcacac atggacacag acccacacat gtttacagaa      1200
ctgttgttta cttgttgctg attcaagaaa c                                     1231

<210> SEQ ID NO 2
<211> LENGTH: 312
<212> TYPE: PRT
<213> ORGANISM: Unknown
<220> FEATURE:
<223> OTHER INFORMATION: Protein UCP3L

<400> SEQUENCE: 2

Met Val Gly Leu Lys Pro Ser Asp Val Pro Thr Met Ala Val Lys
 1               5                  10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
            35                  40                  45

Ala Val Gln Thr Ala Arg Leu Val Gln Tyr Arg Gly Val Leu Gly Thr
        50                  55                  60

Ile Leu Thr Met Val Arg Thr Glu Gly Pro Cys Ser Pro Tyr Asn Gly
 65              70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
```

-continued

```
                130                 135                 140
Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
                180                 185                 190

Asn Cys Ala Glu Val Val Thr Tyr Asp Ile Leu Lys Glu Lys Leu Leu
                195                 200                 205

Asp Tyr His Leu Leu Thr Asp Asn Phe Pro Cys His Phe Val Ser Ala
                210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
                260                 265                 270

Tyr Lys Gly Phe Thr Pro Ser Phe Leu Arg Leu Gly Ser Trp Asn Val
                275                 280                 285

Val Met Phe Val Thr Tyr Glu Gln Leu Lys Arg Ala Leu Met Lys Val
                290                 295                 300

Gln Met Leu Arg Glu Ser Pro Phe
305                 310
```

<210> SEQ ID NO 3
<211> LENGTH: 1132
<212> TYPE: DNA
<213> ORGANISM: Unknown
<220> FEATURE:
<223> OTHER INFORMATION: cDNA from clone UCP3S

<400> SEQUENCE: 3

```
tcctgggatg  gagccctagg  gagcccctgt  gctgcccctg  ccgtggcagg  actcacagcc    60
ccaccgctgc  actgaagccc  agggctgtgg  agcagcctct  ctccttggac  ctcctctcgg   120
ccctaaaggg  actgggcaga  gccttccagg  actatggttg  gactgaagcc  ttcagacgtg   180
cctcccacca  tggctgtgaa  gttcctgggg  gcaggcacag  cagcctgttt  tgctgacctc   240
gttacctttc  cactgacac   agccaaggtc  cgcctgcaga  tccagggga   gaaccaggcg   300
gtccagacgg  cccggctcgt  gcagtaccgt  ggcgtgctgg  gcaccatcct  gaccatggtg   360
cggactgagg  gtccctgcag  ccctacaat   gggctggtgg  ccggcctgca  gcgccagatg   420
agcttcgcct  ccatccgcat  cggcctctat  gactccgtca  gcaggtgta   cacccccaaa   480
ggcgcggaca  actccagcct  cactacccgg  attttggccg  gctgcaccac  aggagccatg   540
gcggtgacct  gtgcccagcc  cacagatgtg  gtgaaggtcc  gatttcaggc  agcatacac   600
ctcgggccat  ccaggagcga  cagaaaatac  agcgggacta  tggacgccta  cagaaccatc   660
gccagggagg  aaggagtcag  gggcctgtgg  aaaggaactt  tgcccaacat  catgaggaat   720
gctatcgtca  actgtgctga  ggtggtgacc  tacgacatcc  tcaaggagaa  gctgctggac   780
taccacctgc  tcactgacaa  cttccccctgc  cactttgtct  ctgcctttgg  agccggcttc   840
tgtgccacag  tggtggcctc  cccggtggac  gtggtgaaga  cccgtatat   gaactcacct   900
ccaggccagt  acttcagccc  cctcgactgt  atgataaaga  tggtggccca  ggagggcccc   960
acagccttct  acaaggggtg  agcctcctcc  tgcctccagc  actccctccc  agagaacagg  1020
```
ggcttctttc ttttcgaatg tggctaccgt gggtcaacct gggatgtagc ggtgaagagt    1080
acagatgtaa atgccacaaa gaagaagttt aaaaaaccat gcaaaaaaaa aa            1132

<210> SEQ ID NO 4
<211> LENGTH: 275
<212> TYPE: PRT
<213> ORGANISM: Unknown
<220> FEATURE:
<223> OTHER INFORMATION: Protein UCP3S

<400> SEQUENCE: 4

Met Val Gly Leu Lys Pro Ser Asp Val Pro Thr Met Ala Val Lys
 1               5                  10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
            35                  40                  45

Ala Val Gln Thr Ala Arg Leu Val Gln Tyr Arg Gly Val Leu Gly Thr
    50                  55                  60

Ile Leu Thr Met Val Arg Thr Glu Gly Pro Cys Ser Pro Tyr Asn Gly
65                  70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
    130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
        195                 200                 205

Asp Tyr His Leu Leu Thr Asp Asn Phe Pro Cys His Phe Val Ser Ala
    210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
            260                 265                 270

Tyr Lys Gly
        275

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 5

-continued

```
gaattcatgc caggcacaaa acgttt                                    27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 6
gtcgactcac tgaacgtcag gctctag                                   27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 7
gaattcatgg cgatggatgt cacaagg                                   27

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 8
gtcgactcac tggcccagca tacagg                                    26

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 9
ctagccaccc acccc                                                15

<210> SEQ ID NO 10
<211> LENGTH: 14
<212> TYPE: DNA
<213> ORGANISM: Artificial Sequence
<220> FEATURE:
<223> OTHER INFORMATION: Oligonucleotide Primer

<400> SEQUENCE: 10
aatggggtgg gtgg                                                 14
```